United States Patent
Perrow et al.

(10) Patent No.: US 11,877,779 B2
(45) Date of Patent: Jan. 23, 2024

(54) BONE PLATE SYSTEM

(71) Applicant: Xtant Medical Holdings, Inc., Belgrade, MT (US)

(72) Inventors: Scott J. Perrow, Ishpeming, MI (US); Michael D. Kakuk, Skandia, MI (US)

(73) Assignee: XTANT MEDICAL HOLDINGS, INC., Belgrade, MT (US)

( * ) Notice: Subject to any disclaimer, the term of this patent is extended or adjusted under 35 U.S.C. 154(b) by 32 days.

(21) Appl. No.: 17/211,489

(22) Filed: Mar. 24, 2021

(65) Prior Publication Data
US 2021/0298804 A1 Sep. 30, 2021

Related U.S. Application Data

(60) Provisional application No. 63/000,163, filed on Mar. 26, 2020.

(51) Int. Cl.
*A61B 17/80* (2006.01)
*A61B 17/88* (2006.01)
*A61B 17/00* (2006.01)

(52) U.S. Cl.
CPC ...... *A61B 17/8047* (2013.01); *A61B 17/8888* (2013.01); *A61B 2017/00526* (2013.01); *A61B 2017/00867* (2013.01)

(58) Field of Classification Search
CPC ............ A61B 17/8047; A61B 17/8033; A61B 17/8042; A61B 2017/00526; A61B 2017/00867
See application file for complete search history.

(56) References Cited

U.S. PATENT DOCUMENTS

| 434,503 A | 8/1890 | Corry |
| 556,642 A | 3/1896 | Reessing |
| (Continued) | | |

FOREIGN PATENT DOCUMENTS

| DE | 251246 | 12/1911 |
| DE | 1949923 | 4/1971 |
| (Continued) | | |

OTHER PUBLICATIONS

Extended European Search Report dated Mar. 17, 2022, in European Application No. 19824755.3 (7 pages).
(Continued)

*Primary Examiner* — Tracy L Kamikawa
(74) *Attorney, Agent, or Firm* — Sheridan Ross P.C.

(57) ABSTRACT

In one aspect, a bone plate system is provided that includes a bone plate body having a throughbore and a bone screw. The bone plate system includes a slider slidably connected to the bone plate body to slide between a clearance position wherein the slider permits a bone screw head portion to be advanced into the throughbore and seated against the bone plate body and an interference position wherein the slider inhibits bone screw back out from the throughbore. The bone plate system includes a resilient pin and the slider has a surface configured to deflect the resilient pin as the bone screw head portion shifts the slider from the interference position toward the clearance position. The deflected resilient pin urges the slider from the clearance position toward the interference position upon the bone anchor head portion seating against the bone plate body in the throughbore.

28 Claims, 19 Drawing Sheets

(56) References Cited

U.S. PATENT DOCUMENTS

| | | |
|---|---|---|
| 872,897 A | 12/1907 | Chapman |
| 951,800 A | 3/1910 | Center |
| 1,084,680 A | 1/1914 | Wegener |
| 1,087,797 A | 2/1914 | Lowe |
| 1,385,780 A | 7/1921 | Dodds |
| 1,409,157 A | 3/1922 | Dodds |
| 1,756,239 A | 4/1930 | Chojnacki |
| 1,907,506 A | 5/1933 | Coburn |
| 1,980,336 A | 11/1934 | Hoagland |
| 2,248,054 A | 7/1941 | Becker |
| 2,376,768 A | 5/1945 | Vasques |
| 2,401,856 A | 6/1946 | Brock |
| 2,580,821 A | 1/1952 | Nicola |
| 2,628,838 A | 2/1953 | Smalley |
| 2,780,223 A | 2/1957 | Haggland |
| 2,877,792 A | 3/1959 | Tybus |
| 3,100,516 A | 8/1963 | Naab |
| 3,244,170 A | 4/1966 | McElvenny |
| 3,426,364 A | 2/1969 | Lumb |
| 3,534,731 A | 10/1970 | Muller |
| 3,596,656 A | 8/1971 | Kaute |
| 3,599,977 A | 8/1971 | Glass |
| 3,604,487 A | 9/1971 | Gilbert |
| 3,659,595 A | 5/1972 | Haboush |
| 3,695,259 A | 10/1972 | Yost |
| 3,710,789 A | 1/1973 | Ersek |
| 3,741,205 A | 6/1973 | Markolf |
| 3,842,825 A | 10/1974 | Wagner |
| 3,844,291 A | 10/1974 | Moen |
| 3,900,025 A | 8/1975 | Barnes, Jr. |
| 3,939,828 A | 2/1976 | Mohr et al. |
| RE28,841 E | 6/1976 | Allgower |
| 4,003,376 A | 1/1977 | McKay |
| 4,029,091 A | 6/1977 | Von |
| 4,334,599 A | 6/1982 | Ritsema |
| RE31,040 E | 9/1982 | Possis |
| 4,361,141 A | 11/1982 | Tanner |
| 4,364,382 A | 12/1982 | Mennen |
| 4,388,921 A | 6/1983 | Sutter |
| RE31,628 E | 7/1984 | Allgower |
| 4,473,068 A | 9/1984 | Oh |
| 4,484,570 A | 11/1984 | Sutter |
| 4,488,543 A | 12/1984 | Tornier |
| 4,493,317 A | 1/1985 | Klaue |
| 4,503,848 A | 3/1985 | Caspar |
| 4,599,086 A | 7/1986 | Doty |
| 4,762,122 A | 8/1988 | Slocum |
| 4,771,767 A | 9/1988 | Steffee |
| 4,776,330 A | 10/1988 | Chapman |
| 4,794,918 A | 1/1989 | Wolter |
| 4,890,845 A | 1/1990 | Gatewood |
| 4,892,545 A | 1/1990 | Day |
| 4,904,261 A | 2/1990 | Dove |
| 4,905,679 A | 3/1990 | Morgan |
| 4,943,292 A | 7/1990 | Foux |
| 4,955,908 A | 9/1990 | Frey |
| 4,957,497 A | 9/1990 | Hoogland |
| 4,964,403 A | 10/1990 | Karas |
| 5,002,544 A | 3/1991 | Klaue |
| 5,020,519 A | 6/1991 | Hayes |
| 5,026,390 A | 6/1991 | Brown |
| 5,041,113 A | 8/1991 | Biedermann |
| 5,041,114 A | 8/1991 | Chapman |
| 5,053,036 A | 10/1991 | Perren |
| 5,057,111 A | 10/1991 | Park |
| 5,085,660 A | 2/1992 | Lin |
| 5,092,320 A | 3/1992 | Maurer |
| 5,092,866 A | 3/1992 | Breard |
| 5,108,395 A | 4/1992 | Laurain |
| 5,113,685 A | 5/1992 | Asher |
| 5,127,912 A | 7/1992 | Ray |
| 5,127,914 A | 7/1992 | Calderale |
| 5,129,899 A | 7/1992 | Small |
| 5,129,903 A | 7/1992 | Luhr |
| 5,139,498 A | 8/1992 | Astudillo Ley |
| 5,139,499 A | 8/1992 | Small |
| 5,147,360 A | 9/1992 | Dubousset |
| 5,147,361 A | 9/1992 | Ojima |
| 5,151,103 A | 9/1992 | Tepic |
| 5,171,279 A | 12/1992 | Mathews |
| 5,180,381 A | 1/1993 | Aust |
| 5,190,544 A | 3/1993 | Chapman |
| 5,234,431 A | 8/1993 | Keller |
| 5,242,443 A | 9/1993 | Kambin |
| 5,258,005 A | 11/1993 | Christian |
| 5,261,910 A | 11/1993 | Warden |
| 5,269,784 A | 12/1993 | Mast |
| 5,275,601 A | 1/1994 | Gogolewski |
| 5,281,226 A | 1/1994 | Davydov et al. |
| 5,304,179 A | 4/1994 | Wagner |
| 5,324,290 A | 6/1994 | Zdeblick |
| 5,326,206 A | 7/1994 | Moore |
| 5,330,535 A | 7/1994 | Moser |
| 5,344,421 A | 9/1994 | Crook |
| 5,346,492 A | 9/1994 | Morgan |
| 5,364,399 A | 11/1994 | Lowery |
| 5,380,323 A | 1/1995 | Howland |
| 5,380,327 A | 1/1995 | Eggers |
| 5,382,248 A | 1/1995 | Jacobson |
| 5,397,363 A | 3/1995 | Gelbard |
| 5,397,364 A | 3/1995 | Kozak |
| 5,415,661 A | 5/1995 | Holmes |
| 5,423,816 A | 6/1995 | Lin |
| 5,423,826 A | 6/1995 | Coates |
| 5,454,769 A | 10/1995 | Chen |
| 5,458,641 A | 10/1995 | Ramirez |
| 5,458,642 A | 10/1995 | Beer et al. |
| 5,468,242 A | 11/1995 | Reisberg |
| 5,478,342 A | 12/1995 | Kohrs |
| 5,480,440 A | 1/1996 | Kambin |
| 5,486,176 A | 1/1996 | Hildebrand |
| 5,501,684 A | 3/1996 | Schlapfer |
| 5,507,772 A | 4/1996 | Shutt |
| 5,520,690 A | 5/1996 | Errico |
| 5,520,696 A | 5/1996 | Wenstrom |
| 5,522,899 A | 6/1996 | Michelson |
| 5,527,311 A | 6/1996 | Procter |
| 5,531,746 A | 7/1996 | Errico |
| 5,534,027 A | 7/1996 | Hodorek |
| 5,534,032 A | 7/1996 | Hodorek |
| 5,549,612 A | 8/1996 | Yapp |
| 5,569,247 A | 10/1996 | Morrison |
| 5,571,109 A | 11/1996 | Bertagnoli |
| 5,578,034 A | 11/1996 | Estes |
| 5,584,887 A | 12/1996 | Kambin |
| 5,601,553 A | 2/1997 | Trebing |
| 5,603,713 A | 2/1997 | Aust |
| 5,607,426 A | 3/1997 | Ralph |
| 5,607,428 A | 3/1997 | Lin |
| 5,616,144 A | 4/1997 | Yapp |
| 5,620,443 A | 4/1997 | Gertzbein et al. |
| 5,626,449 A | 5/1997 | McKinlay |
| 5,643,265 A | 7/1997 | Errico |
| 5,647,872 A | 7/1997 | Gilbert |
| 5,651,651 A | 7/1997 | Spencer |
| 5,653,708 A | 8/1997 | Howland |
| 5,667,513 A | 9/1997 | Torrie |
| 5,676,666 A | 10/1997 | Oxland |
| 5,676,703 A | 10/1997 | Gelbard |
| 5,681,311 A | 10/1997 | Foley |
| 5,681,312 A | 10/1997 | Yuan |
| 5,683,392 A | 11/1997 | Richelsoph |
| 5,683,465 A | 11/1997 | Shinn |
| 5,690,631 A | 11/1997 | Duncan |
| 5,704,936 A | 1/1998 | Mazel |
| 5,707,372 A | 1/1998 | Errico |
| 5,709,686 A | 1/1998 | Talos |
| 5,713,900 A | 2/1998 | Benzel et al. |
| 5,720,751 A | 2/1998 | Jackson |
| 5,725,588 A | 3/1998 | Errico |
| 5,731,275 A | 3/1998 | Prevost |
| 5,735,850 A | 4/1998 | Baumgartner |
| 5,735,853 A | 4/1998 | Olerud |
| 5,735,899 A | 4/1998 | Schwartz |

(56) References Cited

U.S. PATENT DOCUMENTS

| | | |
|---|---|---|
| 5,741,258 A | 4/1998 | Klaue |
| 5,766,176 A | 6/1998 | Duncan |
| 5,766,218 A | 6/1998 | Arnott |
| 5,766,254 A | 6/1998 | Gelbard |
| 5,782,833 A | 7/1998 | Haider |
| 5,785,713 A | 7/1998 | Jobe |
| 5,797,912 A | 8/1998 | Runciman |
| 5,800,433 A | 9/1998 | Benzel |
| 5,807,396 A | 9/1998 | Raveh |
| 5,810,823 A | 9/1998 | Klaue |
| 5,814,048 A | 9/1998 | Morgan |
| 5,827,285 A | 10/1998 | Bramlet |
| 5,840,078 A | 11/1998 | Yerys |
| 5,843,082 A | 12/1998 | Yuan |
| 5,863,293 A | 1/1999 | Richelsoph |
| 5,876,402 A | 3/1999 | Errico |
| 5,879,389 A | 3/1999 | Koshinc |
| 5,888,221 A | 3/1999 | Gelbard |
| 5,904,683 A | 5/1999 | Pohndorf |
| 5,916,200 A | 6/1999 | Eppley |
| 5,941,885 A | 8/1999 | Jackson |
| 5,951,557 A | 9/1999 | Luter |
| 5,951,558 A | 9/1999 | Fiz |
| 5,954,635 A | 9/1999 | Foley et al. |
| 5,954,722 A | 9/1999 | Bono |
| 5,964,760 A | 10/1999 | Richelsoph |
| 5,964,761 A | 10/1999 | Kambin |
| 5,964,762 A | 10/1999 | Biedermann |
| 5,976,141 A | 11/1999 | Haag |
| 5,980,540 A | 11/1999 | Bruce |
| 5,984,924 A | 11/1999 | Asher |
| 6,010,503 A | 1/2000 | Richelsoph |
| 6,017,345 A | 1/2000 | Richelsoph |
| 6,022,350 A | 2/2000 | Ganem |
| 6,030,389 A | 2/2000 | Wagner |
| 6,036,693 A | 3/2000 | Yuan |
| 6,039,740 A | 3/2000 | Olerud |
| 6,090,111 A | 7/2000 | Nichols |
| 6,096,044 A | 8/2000 | Boyd |
| 6,106,557 A | 8/2000 | Robioneck |
| 6,117,135 A | 9/2000 | Schlaepfer |
| 6,117,173 A | 9/2000 | Taddia |
| 6,129,730 A | 10/2000 | Bono |
| 6,132,432 A | 10/2000 | Richelsoph |
| 6,132,434 A | 10/2000 | Sherman |
| 6,136,002 A | 10/2000 | Shih et al. |
| 6,139,550 A | 10/2000 | Michelson |
| 6,152,927 A | 11/2000 | Farris |
| 6,159,213 A | 12/2000 | Rogozinski |
| 6,174,311 B1 | 1/2001 | Branch |
| 6,183,476 B1 | 2/2001 | Gerhardt |
| 6,189,422 B1 | 2/2001 | Stihl |
| 6,193,720 B1 | 2/2001 | Yuan |
| 6,193,721 B1 | 2/2001 | Michelson |
| 6,206,881 B1 | 3/2001 | Frigg |
| 6,206,882 B1 | 3/2001 | Cohen |
| 6,214,005 B1 | 4/2001 | Benzel |
| 6,224,602 B1 | 5/2001 | Hayes |
| 6,226,548 B1 | 5/2001 | Foley |
| 6,228,085 B1 | 5/2001 | Theken |
| 6,235,032 B1 | 5/2001 | Link |
| 6,235,033 B1 | 5/2001 | Brace |
| 6,235,034 B1 | 5/2001 | Bray |
| 6,241,731 B1 | 6/2001 | Fiz |
| 6,254,603 B1 | 7/2001 | Gertzbein |
| 6,257,593 B1 | 7/2001 | White |
| 6,258,089 B1 | 7/2001 | Campbell |
| 6,261,042 B1 | 7/2001 | Pratt |
| 6,261,291 B1 | 7/2001 | Talaber |
| 6,273,889 B1 | 8/2001 | Richelsoph |
| 6,280,445 B1 | 8/2001 | Morrison |
| 6,287,309 B1 | 9/2001 | Baccelli |
| 6,287,313 B1 | 9/2001 | Sasso |
| 6,290,703 B1 | 9/2001 | Ganem |
| 6,293,949 B1 | 9/2001 | Justis |
| D449,692 S | 10/2001 | Michelson |
| 6,306,136 B1 | 10/2001 | Baccelli |
| 6,306,139 B1 | 10/2001 | Fuentes |
| 6,315,779 B1 | 11/2001 | Morrison |
| 6,322,562 B1 | 11/2001 | Wolter |
| 6,328,738 B1 | 12/2001 | Suddaby |
| 6,331,179 B1 | 12/2001 | Freid |
| 6,332,887 B1 | 12/2001 | Knox |
| 6,342,055 B1 | 1/2002 | Eisermann et al. |
| 6,342,057 B1 | 1/2002 | Brace |
| 6,355,040 B1 | 3/2002 | Richelsoph |
| 6,361,537 B1 | 3/2002 | Anderson |
| 6,364,880 B1 | 4/2002 | Michelson |
| 6,379,364 B1 | 4/2002 | Brace |
| 6,381,806 B1 | 5/2002 | Stanesic |
| 6,383,186 B1 | 5/2002 | Michelson |
| 6,398,783 B1 | 6/2002 | Michelson |
| 6,402,206 B1 | 6/2002 | Simmons |
| 6,402,755 B1 | 6/2002 | Pisharodi |
| 6,402,756 B1 | 6/2002 | Ralph |
| 6,402,759 B1 | 6/2002 | Strong |
| 6,406,478 B1 | 6/2002 | Kuo |
| 6,413,259 B1 | 7/2002 | Lyons |
| 6,416,528 B1 | 7/2002 | Michelson |
| 6,423,068 B1 | 7/2002 | Reisberg |
| 6,428,542 B1 | 8/2002 | Michelson |
| 6,440,133 B1 | 8/2002 | Beale |
| 6,454,711 B1 | 9/2002 | Haddad |
| 6,454,769 B2 | 9/2002 | Wagner |
| 6,454,771 B1 | 9/2002 | Michelson |
| 6,458,133 B1 | 10/2002 | Lin |
| 6,471,704 B2 | 10/2002 | Gertzbein |
| 6,478,797 B1 | 11/2002 | Paul |
| 6,485,491 B1 | 11/2002 | Farris |
| 6,485,591 B1 | 11/2002 | Nakao |
| 6,503,250 B2 | 1/2003 | Paul |
| 6,527,776 B1 | 3/2003 | Michelson |
| 6,530,929 B1 | 3/2003 | Justis |
| 6,533,786 B1 | 3/2003 | Needham |
| 6,565,565 B1 | 5/2003 | Yuan |
| 6,572,619 B2 | 6/2003 | Santilli |
| 6,575,975 B2 | 6/2003 | Brace |
| 6,579,290 B1 | 6/2003 | Hardcastle |
| 6,585,769 B1 | 7/2003 | Muhanna |
| 6,592,586 B1 | 7/2003 | Michelson |
| 6,595,993 B2 | 7/2003 | Donno |
| 6,599,290 B2 | 7/2003 | Bailey |
| 6,602,255 B1 | 8/2003 | Campbell |
| 6,602,256 B1 | 8/2003 | Hayes |
| 6,602,257 B1 | 8/2003 | Thramann |
| 6,605,090 B1 | 8/2003 | Trieu |
| 6,613,053 B1 | 9/2003 | Collins |
| 6,613,728 B1 | 9/2003 | Sirianni |
| 6,616,666 B1 | 9/2003 | Michelson |
| 6,620,163 B1 | 9/2003 | Michelson |
| 6,623,486 B1 | 9/2003 | Weaver |
| 6,626,907 B2 | 9/2003 | Campbell |
| 6,627,590 B1 | 9/2003 | Sherry |
| 6,645,207 B2 | 11/2003 | Dixon et al. |
| 6,648,888 B1 | 11/2003 | Shluzas |
| 6,652,525 B1 | 11/2003 | Assaker |
| 6,660,006 B2 | 12/2003 | Markworth |
| 6,663,632 B1 | 12/2003 | Frigg |
| 6,666,866 B2 | 12/2003 | Martz |
| 6,669,700 B1 | 12/2003 | Farris |
| 6,692,503 B2 | 2/2004 | Foley |
| 6,695,846 B2 | 2/2004 | Richelsoph et al. |
| 6,719,793 B2 | 4/2004 | McGee |
| 6,749,614 B2 | 6/2004 | Teitelbaum |
| 6,755,829 B1 | 6/2004 | Bono |
| 6,755,833 B1 | 6/2004 | Paul |
| 6,783,531 B2 | 8/2004 | Allen |
| 6,793,656 B1 | 9/2004 | Mathews |
| 6,860,883 B2 | 3/2005 | Janowski |
| 6,875,212 B2 | 4/2005 | Shaolian |
| 6,890,334 B2 | 5/2005 | Brace |
| 6,890,335 B2 | 5/2005 | Grabowski |
| 6,916,320 B2 | 7/2005 | Michelson |
| 6,951,538 B2 | 10/2005 | Ritland |

(56) References Cited

U.S. PATENT DOCUMENTS

| | | |
|---|---|---|
| 6,964,664 B2 | 11/2005 | Freid |
| 6,964,667 B2 | 11/2005 | Shaolian |
| 6,966,735 B1 | 11/2005 | Yamazaki |
| 6,986,771 B2 | 1/2006 | Paul et al. |
| 6,997,086 B1 | 2/2006 | Graham |
| 7,008,427 B2 | 3/2006 | Sevrain |
| 7,011,660 B2 | 3/2006 | Sherman |
| 7,048,739 B2 | 5/2006 | Konieczynski |
| 7,074,221 B2 | 7/2006 | Michelson |
| 7,081,117 B2 | 7/2006 | Bono |
| 7,083,621 B2 | 8/2006 | Shaolian |
| 7,090,674 B2 | 8/2006 | Doubler |
| 7,125,426 B2 | 10/2006 | Moumene |
| 7,141,051 B2 | 11/2006 | Janowski |
| 7,273,481 B2 | 9/2007 | Lombardo |
| 7,410,496 B2 | 8/2008 | Derouet |
| 7,452,370 B2* | 11/2008 | Anderson ........ A61B 17/8042 606/296 |
| 7,476,239 B2 | 1/2009 | Jackson |
| 7,476,240 B2 | 1/2009 | Raymond |
| 7,591,840 B2 | 9/2009 | Suddaby |
| 7,618,443 B2 | 11/2009 | Abdou |
| 7,635,366 B2 | 12/2009 | Abdou |
| 7,662,175 B2 | 2/2010 | Jackson |
| 7,666,185 B2 | 2/2010 | Ryan |
| 7,682,379 B2 | 3/2010 | Mathieu |
| 7,740,649 B2 | 6/2010 | Mosca |
| 7,749,256 B2 | 7/2010 | Farris et al. |
| 7,763,056 B2 | 7/2010 | Dalton |
| 7,766,915 B2 | 8/2010 | Jackson |
| 7,780,706 B2 | 8/2010 | Marino |
| 7,794,482 B2 | 9/2010 | Mathieu |
| 7,833,256 B2 | 11/2010 | Biedermann et al. |
| 7,854,752 B2 | 12/2010 | Colleran |
| 7,857,836 B2 | 12/2010 | Huebner et al. |
| 7,862,591 B2 | 1/2011 | Dewey |
| 7,875,065 B2 | 1/2011 | Jackson |
| 7,887,569 B2 | 2/2011 | Frigg |
| 7,901,437 B2 | 3/2011 | Jackson |
| 7,909,852 B2 | 3/2011 | Boomer |
| 7,914,561 B2 | 3/2011 | Konieczynski et al. |
| 7,918,878 B2 | 4/2011 | Songer |
| 7,922,727 B2 | 4/2011 | Songer |
| 7,927,359 B2 | 4/2011 | Trautwein |
| 7,931,679 B2 | 4/2011 | Heggeness |
| 7,935,126 B2 | 5/2011 | Orbay |
| 7,942,909 B2 | 5/2011 | Hammill |
| 7,942,910 B2 | 5/2011 | Doubler |
| 7,942,911 B2 | 5/2011 | Doubler |
| 7,947,065 B2 | 5/2011 | Hammill |
| 7,951,170 B2 | 5/2011 | Jackson |
| 7,951,173 B2 | 5/2011 | Hammill |
| 7,951,179 B2 | 5/2011 | Matityahu |
| 7,967,850 B2 | 6/2011 | Jackson |
| 7,972,366 B2 | 7/2011 | Richelsoph et al. |
| 7,993,380 B2 | 8/2011 | Hawkes |
| 8,012,177 B2 | 9/2011 | Jackson |
| 8,025,681 B2 | 9/2011 | Colleran |
| 8,043,346 B2 | 10/2011 | Markworth |
| 8,192,439 B2 | 6/2012 | Songer |
| 8,216,285 B2 | 7/2012 | Markworth |
| 8,226,693 B2 | 7/2012 | Reimels et al. |
| 8,257,404 B2 | 9/2012 | Hack |
| 8,262,711 B2 | 9/2012 | Hess |
| 8,361,126 B2 | 1/2013 | Perrow |
| 8,500,737 B2 | 8/2013 | Richelsoph et al. |
| 8,551,141 B2 | 10/2013 | Gephart |
| 8,562,656 B2* | 10/2013 | Humphreys ....... A61B 17/8033 606/289 |
| 8,574,270 B2 | 11/2013 | Hess et al. |
| 8,585,742 B2 | 11/2013 | Windolf |
| 8,623,019 B2 | 1/2014 | Perrow et al. |
| 8,641,719 B2 | 2/2014 | Gephart |
| 8,728,127 B2 | 5/2014 | Stewart |
| 8,747,441 B2 | 6/2014 | Konieczynski et al. |
| 8,758,347 B2 | 6/2014 | Weiner et al. |
| 8,790,379 B2 | 7/2014 | Bottlang et al. |
| 8,814,915 B2 | 8/2014 | Hess et al. |
| 8,882,812 B2 | 11/2014 | Hess et al. |
| 8,882,815 B2 | 11/2014 | Bottlang et al. |
| 8,906,077 B2* | 12/2014 | Bush, Jr. ............ A61B 17/8042 606/281 |
| 8,932,335 B2* | 1/2015 | Humphreys ....... A61B 17/7059 606/294 |
| 8,940,030 B1 | 1/2015 | Stein et al. |
| 8,974,504 B2 | 3/2015 | Hess et al. |
| 8,992,583 B2 | 3/2015 | Bottlang et al. |
| 9,005,255 B2 | 4/2015 | Lewis et al. |
| 9,005,257 B2 | 4/2015 | Sun |
| 9,033,988 B2 | 5/2015 | Gephart et al. |
| 9,095,388 B2 | 8/2015 | Hess et al. |
| 9,198,769 B2 | 12/2015 | Perrow et al. |
| 9,265,531 B2* | 2/2016 | Ziolo ................. A61B 17/7059 |
| 9,295,503 B2 | 3/2016 | Frigg et al. |
| 9,295,508 B2 | 3/2016 | Bottlang et al. |
| 9,326,803 B2 | 5/2016 | Humphreys |
| 9,351,774 B2 | 5/2016 | Konieczynski et al. |
| 9,381,046 B2 | 7/2016 | Perrow et al. |
| 9,408,647 B2 | 8/2016 | Cheney |
| 9,498,259 B2 | 11/2016 | Dirisio et al. |
| 9,510,879 B2 | 12/2016 | Bottlang et al. |
| 9,579,135 B2 | 2/2017 | Cook et al. |
| 9,700,361 B2 | 7/2017 | Bottlang et al. |
| 9,763,713 B2 | 9/2017 | Bottlang et al. |
| 9,788,863 B2 | 10/2017 | Juchno et al. |
| 9,788,873 B2 | 10/2017 | Bottlang et al. |
| 9,855,082 B2 | 1/2018 | Hulliger et al. |
| 9,883,897 B2 | 2/2018 | Taber |
| 9,918,759 B2* | 3/2018 | Paul ................... A61B 17/8042 |
| 9,924,987 B2 | 3/2018 | Cheney |
| 10,022,168 B2 | 7/2018 | Bottlang et al. |
| 10,070,905 B2 | 9/2018 | Bottlang et al. |
| 10,092,336 B2 | 10/2018 | Hess et al. |
| 10,123,831 B2 | 11/2018 | Gephart |
| 10,159,514 B2 | 12/2018 | Perrow et al. |
| 10,166,051 B2 | 1/2019 | Perrow |
| 10,226,291 B2 | 3/2019 | Perrow et al. |
| 10,898,247 B2 | 1/2021 | Perrow |
| 11,344,346 B2 | 5/2022 | Gephart |
| 2001/0014807 A1 | 8/2001 | Wagner |
| 2001/0021851 A1 | 9/2001 | Eberlein |
| 2001/0037112 A1 | 11/2001 | Brace |
| 2001/0041894 A1 | 11/2001 | Campbell |
| 2001/0047172 A1 | 11/2001 | Foley |
| 2001/0047174 A1 | 11/2001 | Donno |
| 2002/0013586 A1 | 1/2002 | Justis |
| 2002/0016595 A1 | 2/2002 | Michelson |
| 2002/0022843 A1 | 2/2002 | Michelson |
| 2002/0029040 A1 | 3/2002 | Morrison |
| 2002/0045896 A1 | 4/2002 | Michelson |
| 2002/0045898 A1 | 4/2002 | Freid |
| 2002/0045899 A1 | 4/2002 | Errico |
| 2002/0049444 A1 | 4/2002 | Knox |
| 2002/0058939 A1 | 5/2002 | Wagner |
| 2002/0065517 A1 | 5/2002 | Paul |
| 2002/0068938 A1 | 6/2002 | Jackson |
| 2002/0077630 A1 | 6/2002 | Lin |
| 2002/0111630 A1 | 8/2002 | Ralph |
| 2002/0120268 A1 | 8/2002 | Berger |
| 2002/0120271 A1 | 8/2002 | Dixon |
| 2002/0120272 A1 | 8/2002 | Yuan |
| 2002/0120273 A1 | 8/2002 | Needham |
| 2002/0128654 A1 | 9/2002 | Steger |
| 2002/0128655 A1 | 9/2002 | Michelson |
| 2002/0151893 A1 | 10/2002 | Santilli |
| 2002/0151899 A1 | 10/2002 | Bailey |
| 2002/0151900 A1 | 10/2002 | Glascott |
| 2002/0156474 A1 | 10/2002 | Wack |
| 2002/0161368 A1 | 10/2002 | Foley |
| 2002/0161370 A1 | 10/2002 | Frigg |
| 2002/0173790 A1 | 11/2002 | Chang |
| 2002/0183747 A1 | 12/2002 | Jao |
| 2002/0183754 A1 | 12/2002 | Michelson |
| 2002/0183755 A1 | 12/2002 | Michelson |

(56) References Cited

U.S. PATENT DOCUMENTS

| | | |
|---|---|---|
| 2002/0183756 A1 | 12/2002 | Michelson |
| 2002/0183757 A1 | 12/2002 | Michelson |
| 2002/0188296 A1 | 12/2002 | Michelson |
| 2003/0004519 A1 | 1/2003 | Torode |
| 2003/0018335 A1 | 1/2003 | Michelson |
| 2003/0023242 A1 | 1/2003 | Harrington |
| 2003/0040749 A1 | 2/2003 | Grabowski |
| 2003/0045880 A1 | 3/2003 | Michelson |
| 2003/0060826 A1 | 3/2003 | Foley |
| 2003/0060828 A1 | 3/2003 | Michelson |
| 2003/0073998 A1 | 4/2003 | Pagliuca |
| 2003/0078583 A1 | 4/2003 | Biedermann |
| 2003/0093082 A1 | 5/2003 | Campbell |
| 2003/0105462 A1 | 6/2003 | Haider |
| 2003/0125742 A1 | 7/2003 | Yuan |
| 2003/0130661 A1 | 7/2003 | Osman |
| 2003/0149434 A1 | 8/2003 | Paul |
| 2003/0153920 A1 | 8/2003 | Ralph |
| 2003/0167058 A1 | 9/2003 | Shluzas |
| 2003/0181912 A1 | 9/2003 | Michelson |
| 2003/0187440 A1 | 10/2003 | Richelsoph |
| 2003/0187441 A1 | 10/2003 | Bolger |
| 2003/0187442 A1 | 10/2003 | Richelsoph |
| 2003/0187509 A1 | 10/2003 | Lemole |
| 2003/0191471 A1 | 10/2003 | Michelson |
| 2003/0191472 A1 | 10/2003 | Michelson |
| 2003/0208203 A1 | 11/2003 | Lim |
| 2003/0208204 A1 | 11/2003 | Bailey |
| 2003/0225408 A1 | 12/2003 | Nichols |
| 2003/0225409 A1 | 12/2003 | Freid |
| 2003/0229347 A1 | 12/2003 | Sherman |
| 2003/0236447 A1 | 12/2003 | Ritland |
| 2004/0019353 A1 | 1/2004 | Freid |
| 2004/0030338 A1 | 2/2004 | Paul |
| 2004/0039384 A1 | 2/2004 | Boehm |
| 2004/0039388 A1 | 2/2004 | Biedermann et al. |
| 2004/0059333 A1 | 3/2004 | Carl |
| 2004/0068319 A1 | 4/2004 | Cordaro |
| 2004/0082960 A1 | 4/2004 | Davison |
| 2004/0087951 A1 | 5/2004 | Khalili |
| 2004/0087955 A1 | 5/2004 | Bordi |
| 2004/0092938 A1 | 5/2004 | Carli |
| 2004/0092952 A1 | 5/2004 | Newton |
| 2004/0097934 A1 | 5/2004 | Farris |
| 2004/0097935 A1 | 5/2004 | Richelsoph |
| 2004/0097950 A1 | 5/2004 | Foley |
| 2004/0116931 A1 | 6/2004 | Carlson |
| 2004/0122426 A1 | 6/2004 | Michelson |
| 2004/0127896 A1 | 7/2004 | Lombardo |
| 2004/0127897 A1 | 7/2004 | Freid |
| 2004/0127899 A1 | 7/2004 | Konieczynski |
| 2004/0127900 A1 | 7/2004 | Konieczynski |
| 2004/0133201 A1 | 7/2004 | Shluzas et al. |
| 2004/0138662 A1 | 7/2004 | Landry |
| 2004/0143265 A1 | 7/2004 | Landry |
| 2004/0147928 A1 | 7/2004 | Landry et al. |
| 2004/0147937 A1 | 7/2004 | Dunbar |
| 2004/0158246 A1 | 8/2004 | Assaker |
| 2004/0172022 A1 | 9/2004 | Landry |
| 2004/0186482 A1 | 9/2004 | Kolb |
| 2004/0204710 A1 | 10/2004 | Patel |
| 2004/0204716 A1 | 10/2004 | Fanger |
| 2004/0204717 A1 | 10/2004 | Fanger |
| 2004/0215190 A1 | 10/2004 | Nguyen |
| 2004/0220570 A1 | 11/2004 | Frigg |
| 2004/0220571 A1 | 11/2004 | Assaker et al. |
| 2004/0230100 A1 | 11/2004 | Shluzas |
| 2004/0230191 A1 | 11/2004 | Frey |
| 2004/0236334 A1 | 11/2004 | Michelson |
| 2005/0004519 A1 | 1/2005 | Vanjaarsveldt |
| 2005/0004573 A1 | 1/2005 | Abdou |
| 2005/0004593 A1 | 1/2005 | Simonson |
| 2005/0021030 A1 | 1/2005 | Pagliuca |
| 2005/0021031 A1 | 1/2005 | Foley |
| 2005/0033297 A1 | 2/2005 | Davison |
| 2005/0033298 A1 | 2/2005 | Hawkes |
| 2005/0033299 A1 | 2/2005 | Shluzas |
| 2005/0038436 A1 | 2/2005 | Michelson |
| 2005/0043732 A1 | 2/2005 | Dalton |
| 2005/0049593 A1 | 3/2005 | Duong |
| 2005/0065516 A1 | 3/2005 | Jahng |
| 2005/0065517 A1 | 3/2005 | Chin |
| 2005/0075540 A1 | 4/2005 | Shluzas |
| 2005/0075644 A1 | 4/2005 | DiPoto |
| 2005/0080418 A1 | 4/2005 | Simonson |
| 2005/0085813 A1 | 4/2005 | Spitler |
| 2005/0090822 A1 | 4/2005 | DiPoto |
| 2005/0090824 A1 | 4/2005 | Shluzas |
| 2005/0090833 A1 | 4/2005 | DiPoto |
| 2005/0090899 A1 | 4/2005 | DiPoto |
| 2005/0107789 A1 | 5/2005 | Sweeney |
| 2005/0131408 A1 | 6/2005 | Sicvol |
| 2005/0131419 A1 | 6/2005 | McCord |
| 2005/0131420 A1 | 6/2005 | Techiera |
| 2005/0131421 A1 | 6/2005 | Anderson |
| 2005/0131422 A1 | 6/2005 | Anderson |
| 2005/0137593 A1 | 6/2005 | Gray |
| 2005/0149022 A1 | 7/2005 | Shaolian |
| 2005/0149036 A1 | 7/2005 | Varieur |
| 2005/0149053 A1 | 7/2005 | Varieur |
| 2005/0154389 A1 | 7/2005 | Selover |
| 2005/0154392 A1 | 7/2005 | Medoff |
| 2005/0159651 A1 | 7/2005 | Raymond et al. |
| 2005/0171540 A1 | 8/2005 | Lim |
| 2005/0171551 A1 | 8/2005 | Sukovich |
| 2005/0192570 A1 | 9/2005 | Jackson |
| 2005/0192577 A1 | 9/2005 | Mosca |
| 2005/0192579 A1 | 9/2005 | Jackson |
| 2005/0192589 A1 | 9/2005 | Raymond |
| 2005/0203513 A1 | 9/2005 | Jahng et al. |
| 2005/0215999 A1 | 9/2005 | Birkmeyer |
| 2005/0216002 A1 | 9/2005 | Simonson |
| 2005/0228380 A1 | 10/2005 | Moore |
| 2005/0228400 A1 | 10/2005 | Chao |
| 2005/0234456 A1 | 10/2005 | Malandain |
| 2005/0245942 A1 | 11/2005 | DiPoto |
| 2005/0251192 A1 | 11/2005 | Shluzas |
| 2005/0273131 A1 | 12/2005 | Shluzas |
| 2005/0273132 A1 | 12/2005 | Shluzas |
| 2005/0273133 A1 | 12/2005 | Shluzas |
| 2005/0288671 A1 | 12/2005 | Yuan |
| 2006/0036244 A1 | 2/2006 | Spitler |
| 2006/0074445 A1 | 4/2006 | Gerber et al. |
| 2006/0079900 A1 | 4/2006 | Mathieu |
| 2006/0089651 A1 | 4/2006 | Trudeau |
| 2006/0106387 A1 | 5/2006 | Fanger |
| 2006/0111714 A1 | 5/2006 | Foley |
| 2006/0122602 A1 | 6/2006 | Konieczynski |
| 2006/0122604 A1 | 6/2006 | Gorhan |
| 2006/0149256 A1 | 7/2006 | Wagner |
| 2006/0155278 A1 | 7/2006 | Warnick |
| 2006/0161157 A1 | 7/2006 | Mosca |
| 2006/0167457 A1 | 7/2006 | Suddaby |
| 2006/0167547 A1 | 7/2006 | Suddaby |
| 2006/0173456 A1 | 8/2006 | Hawkes |
| 2006/0200132 A1 | 9/2006 | Chao |
| 2006/0200135 A1 | 9/2006 | Sherman |
| 2006/0200147 A1 | 9/2006 | Ensign |
| 2006/0217725 A1 | 9/2006 | Suh |
| 2006/0229614 A1 | 10/2006 | Foley |
| 2006/0235393 A1 | 10/2006 | Bono |
| 2006/0235399 A1 | 10/2006 | Carls |
| 2006/0241600 A1 | 10/2006 | Ensign |
| 2006/0241616 A1 | 10/2006 | Konieczynski |
| 2006/0247630 A1 | 11/2006 | Iott |
| 2006/0247636 A1 | 11/2006 | Yuan |
| 2006/0247639 A1 | 11/2006 | Anderson |
| 2006/0264962 A1 | 11/2006 | Chin |
| 2006/0276791 A1 | 12/2006 | Shluzas |
| 2006/0276792 A1 | 12/2006 | Ensign |
| 2007/0010817 A1 | 1/2007 | De Coninck |
| 2007/0055235 A1 | 3/2007 | Janowski |
| 2007/0055251 A1 | 3/2007 | Huebner et al. |
| 2007/0078460 A1 | 4/2007 | Frigg |

(56) References Cited

U.S. PATENT DOCUMENTS

| | | |
|---|---|---|
| 2007/0093817 A1 | 4/2007 | Barrus |
| 2007/0093826 A1 | 4/2007 | Hawkes |
| 2007/0093827 A1 | 4/2007 | Warnick |
| 2007/0123879 A1 | 5/2007 | Songer |
| 2007/0162016 A1 | 7/2007 | Matityahu |
| 2007/0185491 A1 | 8/2007 | Foley |
| 2007/0198015 A1 | 8/2007 | Foley |
| 2007/0213714 A1 | 9/2007 | Justis |
| 2007/0213727 A1 | 9/2007 | Bottlang et al. |
| 2007/0225711 A1 | 9/2007 | Ensign |
| 2007/0288004 A1 | 12/2007 | Alvarez |
| 2008/0015591 A1 | 1/2008 | Castaneda |
| 2008/0027439 A1 | 1/2008 | Sasing |
| 2008/0039840 A1 | 2/2008 | Songer |
| 2008/0140129 A1 | 6/2008 | Dalton |
| 2008/0147124 A1 | 6/2008 | Haidukewych et al. |
| 2008/0154277 A1 | 6/2008 | Machalk |
| 2008/0172094 A1 | 7/2008 | Mathieu |
| 2008/0177330 A1 | 7/2008 | Ralph |
| 2008/0195155 A1 | 8/2008 | Hoffman |
| 2008/0228233 A1 | 9/2008 | Hoffman |
| 2008/0243133 A1 | 10/2008 | Heinz |
| 2008/0269753 A1 | 10/2008 | Cannestra |
| 2008/0306550 A1 | 12/2008 | Matityahu |
| 2009/0012571 A1 | 1/2009 | Perrow |
| 2009/0024170 A1 | 1/2009 | Kirschman |
| 2009/0038446 A1 | 2/2009 | Ensign |
| 2009/0062862 A1 | 3/2009 | Perrow |
| 2009/0069812 A1 | 3/2009 | Gillard et al. |
| 2009/0228054 A1 | 9/2009 | Hoffman |
| 2010/0036430 A1 | 2/2010 | Hartdegen et al. |
| 2010/0063505 A1 | 3/2010 | Frigg et al. |
| 2010/0160977 A1 | 6/2010 | Gephart |
| 2011/0106182 A1 | 5/2011 | Reisberg |
| 2011/0112584 A1 | 5/2011 | Frigg |
| 2011/0295324 A1 | 12/2011 | Donley et al. |
| 2012/0221061 A1 | 8/2012 | Peppers |
| 2012/0296440 A1 | 11/2012 | Choux et al. |
| 2013/0090695 A1 | 4/2013 | Bernstein et al. |
| 2013/0131685 A1 | 5/2013 | Perrow |
| 2013/0190762 A1 | 7/2013 | Frankle et al. |
| 2013/0304067 A1 | 11/2013 | Hess et al. |
| 2014/0039630 A1 | 2/2014 | Peyrot et al. |
| 2014/0066997 A1 | 3/2014 | Humphreys |
| 2014/0128924 A1 | 5/2014 | Perrow et al. |
| 2014/0188178 A1 | 7/2014 | Juchno et al. |
| 2015/0157374 A1 | 6/2015 | Gephart et al. |
| 2015/0230843 A1 | 8/2015 | Palmer et al. |
| 2015/0238238 A1 | 8/2015 | Cheney |
| 2015/0289918 A1 | 10/2015 | Burckhardt et al. |
| 2015/0313656 A1 | 11/2015 | Hulliger |
| 2016/0074082 A1 | 3/2016 | Cremer et al. |
| 2016/0157905 A1 | 6/2016 | Arellano et al. |
| 2016/0166296 A9 | 6/2016 | Juchno et al. |
| 2016/0256203 A1 | 9/2016 | Gephart |
| 2016/0270831 A1 | 9/2016 | Perrow et al. |
| 2017/0196606 A1* | 7/2017 | Cianfrani ............ A61B 17/8042 |
| 2017/0360487 A1 | 12/2017 | Moseley et al. |
| 2018/0000520 A1 | 1/2018 | Juchno et al. |
| 2018/0036048 A1 | 2/2018 | Bottlang et al. |
| 2018/0070997 A1 | 3/2018 | Bottlang et al. |
| 2018/0078296 A1 | 3/2018 | Hulliger et al. |
| 2019/0046247 A1 | 2/2019 | Gephart |
| 2019/0175234 A1 | 6/2019 | Perrow et al. |
| 2019/0328427 A1* | 10/2019 | Wolfe ................ A61B 17/8014 |
| 2020/0000501 A1 | 1/2020 | Gephart |

FOREIGN PATENT DOCUMENTS

| | | |
|---|---|---|
| DE | 2933141 | 4/1980 |
| DE | 3808937 | 10/1989 |
| DE | 4409833 | 10/1995 |
| DE | 19548395 | 9/1997 |
| EP | 0179695 | 4/1986 |
| EP | 0201024 | 11/1986 |
| EP | 0242842 | 10/1987 |
| EP | 0251583 | 1/1988 |
| EP | 0410309 | 1/1991 |
| EP | 0455255 | 11/1991 |
| EP | 0471418 | 2/1992 |
| EP | 0502815 | 9/1992 |
| EP | 0599640 | 6/1994 |
| EP | 0699057 | 3/1996 |
| EP | 0767631 | 4/1997 |
| EP | 0809971 | 12/1997 |
| EP | 0809972 | 12/1997 |
| EP | 0828459 | 3/1998 |
| EP | 0874595 | 11/1998 |
| EP | 0876128 | 11/1998 |
| EP | 0897697 | 2/1999 |
| EP | 0903113 | 3/1999 |
| EP | 0988833 | 3/2000 |
| EP | 0995404 | 4/2000 |
| EP | 0999796 | 5/2000 |
| EP | 1106114 | 6/2001 |
| EP | 1106144 | 6/2001 |
| EP | 1169971 | 1/2002 |
| EP | 1185210 | 3/2002 |
| EP | 1220645 | 7/2002 |
| EP | 1285632 | 2/2003 |
| EP | 1306058 | 5/2003 |
| EP | 1336383 | 8/2003 |
| EP | 1340468 | 9/2003 |
| EP | 1346697 | 9/2003 |
| EP | 1364623 | 11/2003 |
| EP | 1561429 | 1/2008 |
| FR | 2435243 | 4/1980 |
| FR | 2519857 | 7/1983 |
| FR | 2556583 | 6/1985 |
| FR | 2726461 | 5/1996 |
| FR | 2740321 | 4/1997 |
| FR | 2794963 | 12/2000 |
| FR | 2810532 | 12/2001 |
| SU | 1424824 | 9/1988 |
| WO | 198803781 | 6/1988 |
| WO | 9103994 | 4/1991 |
| WO | 9417744 | 8/1994 |
| WO | 9525474 | 9/1995 |
| WO | 9531941 | 11/1995 |
| WO | 9600530 | 1/1996 |
| WO | 9605778 | 2/1996 |
| WO | 199608206 | 3/1996 |
| WO | 9629948 | 10/1996 |
| WO | 9632071 | 10/1996 |
| WO | 199639975 | 12/1996 |
| WO | 199722306 | 6/1997 |
| WO | 199834553 | 8/1998 |
| WO | 199834556 | 8/1998 |
| WO | 199851226 | 11/1998 |
| WO | 9904718 | 2/1999 |
| WO | 9921502 | 5/1999 |
| WO | 9956653 | 11/1999 |
| WO | 9959492 | 11/1999 |
| WO | 200003653 | 1/2000 |
| WO | 0025689 | 5/2000 |
| WO | 0062693 | 10/2000 |
| WO | 200066011 | 11/2000 |
| WO | 200078238 | 12/2000 |
| WO | 0101874 | 1/2001 |
| WO | 0126567 | 4/2001 |
| WO | 200126566 | 4/2001 |
| WO | 200149191 | 7/2001 |
| WO | 0164144 | 9/2001 |
| WO | 0182804 | 11/2001 |
| WO | 0182805 | 11/2001 |
| WO | 0189400 | 11/2001 |
| WO | 0189428 | 11/2001 |
| WO | 02076317 | 10/2002 |
| WO | 02080789 | 10/2002 |
| WO | 02098276 | 12/2002 |
| WO | 02098277 | 12/2002 |
| WO | 03007826 | 1/2003 |
| WO | 03017856 | 3/2003 |
| WO | 03053262 | 7/2003 |

(56) References Cited

FOREIGN PATENT DOCUMENTS

| WO | 2003063714 | | 8/2003 |
|---|---|---|---|
| WO | 03071966 | | 9/2003 |
| WO | 2004017847 | A2 | 3/2004 |
| WO | 2004047650 | | 6/2004 |
| WO | 2004071339 | | 8/2004 |
| WO | 2006091863 | | 8/2006 |
| WO | 2008024937 | | 2/2008 |
| WO | 2012162733 | | 12/2012 |

OTHER PUBLICATIONS

F. Paris, V. Tarazona, E. Blasco, A. Canto, M. Casillas, J. Pastor, M. Paris, and R. Montero, Surgical stabilization of traumatic flail chest, Thorax (1975), 30, pp. 521-527.

Charlotte Claw Compression Plate, Wright Medical Technology, Inc., 2 pages, 2015.

Gephart, Matthew P., Bone Plate System, U.S. Appl. No. 62/692,464, filed Jun. 29, 2018.

Johnson Matthey Medical Components, How Does Nitinol Work? All About Nitinol Shape Memory and Superelasticity, retrieved on Jun. 21, 2018; http://jmmedical.com/resources/122/How-Does-Nitinol-Work%3F-All-About-Nitinol-Shape-Memory-and-Superelasticity.html; 2 pages.

Foley, M.D., Kevin T.; Schwender, MD., James D., and Rouben, MD., David P., PyrametriX.RTM. Advance: Instrument Set Technique, surgical brochure provided by manufacturer Medtronic Sofamor Danek, Inc., 2005, (25 pages).

Caspar W; Barbier DD; Klara PM; Abstract: Anterior cervical fusion and Caspar plate stabilization for cervical trauma, Neurosurgery, 1989, Oct. 25(4):491-502 (1page).

Moftakhar, Roham, MD; Trost, Gregory, MD. Anterior Cervical Plates: A Historical Perspective. Neurosurgical Focus, vol. 16, No. 1. Jan. 2004. American Association of Neurological Surgeons; Charlottesville, VA, USA. 5 pages.

Omeis et al., "History of Instrumentation for Stabilization of the Subaxial Cervical Spine," Neurosurg Focus 16 (1): Article 10, 2004.

Chang, J.H.; Chang, G.L.; Hsu, A.T.. Kinematic Study of Cervical Vertebrae Adjacent to Fixation Procedures. 1999 Bioengineering Conference, Big Sky, Montana, USA. Jun. 1999. 2 pages.

Paramore, Christopher, MD; Dickman, Curtis, MD; Sonntag, Volker, MD. Radiographic and Clinical Follow-Up Review of Caspar Plates in 49 Patents. Journal of Neurosurgery, vol. 84, No. 6. Jun. 1996. 5 pages. American Association of Neurological Surgeons; Rolling Meadows, IL, USA.

Clausen, John; Tyken, Timothy, MD; Traynelis, Vincent, MD; Sawin, Paul, MD; Dexter, Franklin, MD; Goel, Vijay. Biomechanical Evaluation of Caspar and Cervical Spine Locking Plate Systems in a Cadaveric Model. Journal of Neurosurgery, vol. 84, No. 6. Jun. 1996. 9 pages. American Association of Neurological Surgeons; Rolling Meadows, IL, USA.

Bose, Bikash, MD. Anterior Cervical Fusion Using Caspar Plating: Analysis of Results and Review of the Literature. Surgical Neurology, vol. 29, No. 1. Jan. 1998. 8 pages. Elsevier Biomedical; New York, NY, USA.

Pitzen, T.; Steudel, W.; Oxland, T. The Effect of Posterior Element Injury on Cervical Spine Flexibility While Using Anterior Plates With and Without Posterior Fixation. An In Vitro Trauma Model. 52nd Annual Meeting of the German Society of Neurosurgery, Bielefeld, Germany. May 2001. 1 page.

Armstrong, Gordon; Chow, Donald. The Contoured Anterior Spinal Plate. Spinal Instrumentation. 1992. Williams & Wilkins; Baltimore, MD, USA.

Zdeblick, Thomas, MD; Ghanayem, Alexander, MD; Rapoff, Andrew, MS; Swain, Carol, MS; Bassett, Tim, MD; Cooke, Mary, MS; Markel, Mark, DVM. Cervical Interbody Fusion Cages: An Animal Model With and Without Bone Morphogenetic Protein. Spine, vol. 23, No. 7., 1998. Lippincott Williams & Wilkins; Hagerstown, MD, USA. 8 pages.

Takahashi, Toshiyuki; Tominaga, Teiji; Yoshimoto, Takashi; Koshu, Keiji; Tokobori, A. Toshimitsu; Aizawa, Yoichi. Biomechanical Evaluation of Hydroxyapatite Intervertebral Graft and Anterior Cervical Plating in a Porcine Cadaveric Model. Bio-medical Materials and Engineering, vol. 7, No. 2. 1997. IOS Press; Amsterdam, Netherlands. 7 pages.

Chen, Ing-Ho, Yang, Rong-Sen, Chen, Po-Quang. Plate Fixation for Anterior Cervical Interbody Fusion. Journal of the Formosan Medical Association, vol. 90, No. 2. Feb. 1991. Scientific Communications International, Hong Kong, China. 4 pages.

Benzel, Edward, MD; Leon, Steven, MD. Enhancing Cervical Spine Fusion, www.medscape.com. Mar. 2001. 31 pages.

Archon Reconstruction System, Technique Guide, NuVasive Speed of Innovation, copyright 2015, San Diego, CA (28 pages).

NuVasive Helix ACP Surgical Technique, Simplicity when you want it. Security when you need it., NuVasive Creative Spine Technology, copyright 2008, San Diego, CA (23 pages).

Assure, Cervical Plate System, Globus Medical, copyright 2006, Audubon, PA (2 pages).

Gradient Plus, Fixed, Semi-Constrained, Translational—All in One Set. A Construct for Every Contingency., NuVasive Creative Spine Technology, copyright 2006, San Diego, CA (36 pages).

White Pearl, Preferred Angle Anterior Cervical Plate, Surgical Technique Guide 2017, Osseus, Dallas TX (15 pages).

Uniplate2, Anterior Cervical Plate System, Surgical Technique Guide and Ordering Information, DePuy Spine, copyright 2010, Raynham, MA (20 pages).

Trinica and Trinica Select Anterior Cervical Plate System, Surgical Technique, Zimmer Spine, copyright 2013, Minneapolis, MN (32 pages).

John P. Kostuik, MD, Pyrenees Surgical Technique, Constrained & Translational, Complex Spine Innovations, copyright 2015, Leesburg, VA (25 pages).

Synthes Spine, Vectra, Vectra-T and Vectra-One Technique Guide, copyright 2010, West Chester, PA (34 pages).

Spider, Cervical Plating System, Revolutionary Locking: Audible, Tactile & Visual, X-spine Systems, copyright 2016, Miamisburg, OH (2 pages).

Snowcap, Anterior Cervical Plate, Surgical Technique Guide, BIOMET Spine, copyright 2014, Broomfield, CO (20 pages).

Skyline, Anterior Cervical Plate System, Surgical Technique & Ordering Information, DePuy Spine, copyright 2010 (24 pages).

Providence, Anterior Cervical Plate System, Globus Medical, copyright 2009, Audubon, PA (2 pages).

Zevo, Anterior Cervical Plate System, Product Information, Medtronic, copyright 2015, Memphis, TN (7 pages).

MaxAn, Anterior Cervical Fixation System, Zimmer Biomet, copyright 2016 (8 pages).

NuVasive Helix Mini ACP, NuVasive Speed of Innovation, copyright 2013, San Diego, CA (3 pages).

Vectra-T, The Translational Anterior Cervical Palate System, Surgical Technique, DePuy Synthes Spine, 2016, Oberdorf, Switzerland (36 pages).

Vectra, Anterior cervical plate system, Surgical Technique, DePuy Synthes Spine, 2016, Oberdorf, Switzerland (28 pages).

Tempus, Anterior Cervical Plate System, Surgical Technique, Stryker Spine, copyright 2016, Allendale, NJ (24 pages).

Reflex Hybrid, Anterior Cervical Plate System, Surgical Technique, Stryker Spine, copyright 2016, Allendale, NJ (24 pages).

Aviator, Anterior Cervical Plate System, Surgical Technique, Stryker Spine, copyright 2016, Allendale, NJ (24 pages).

Ambassador, Anterior Cervical Plate System, Optimal Anatomic Compatibility Versatility Variety, Surgical Technique, ChoiceSpine Propelling Spinal Surgery, 2017, Knoxville, TN (20 pages).

Altantis Vision Elite, Anterior Cervical Plate System, Product Information, Medtronic, copyright 2010, Memphis, TN (16 pages).

Aranax, Cervical Plating System, X-spine Systems, copyright 2016, Miamisburg, OH (2 pages).

Volker K. H. Sonntag, M.D. et al., Atlantis, Anterior Cervical Plate System Surgical Technique, Medtronic, copyright 2002, Memphis, TN (39 pages).

Ascential, ACP 1 Anterior Cervical Plate System, Surgical Technique, Stryker Spine, copyright 2016, Allendale, NJ (24 pages).

(56) References Cited

OTHER PUBLICATIONS

InViZia, Anterior Cervical Plate System, Surgical Technique Guide, Zimmer Biomet, copyright 2017, Westminster, CO (28 pages).
Trestle Luxe, Anterior Cervical Plating System, Surgical Technique Guide, Alphatec Spine, copyright 2012, Carlsbad, CA (20 pages).
Sapphire Anterior Cervical Plate System, Spinal Elements, copyright 2017, Carlsbad, CA (4 pages).
Reliant, Anterior Cervical Plating (ACP) System, Reliant Operative Technique, Orthofix, copyright 2011, Lewisville, TX (16 pages).
Hallmark, Anterior Cervical Plating (ACP) System, Hallmark Operative Technique, Orthofix, copyright 2011, Lewisville, TX (16 pages).
Cetra, Anterior Cervical Plate System, Operative Technique, Orthofix, copyright 2017, Lewisville, TX (20 pages).
3°, Anterior Cervical Plating System, Operative Technique, Orthofix, copyright 2017, Lewisville, TX (18 pages).
U.S. Non-final Office Action dated Jun. 22, 2020, in U.S. Appl. No. 16/164,899, (7 pages).
Archon, Technique Guide, NuVasive Speed of Innovation, copyright 2015, San Diego, CA (24 pages).
International Search Report and Written Opinion dated Jun. 23, 2021, in corresponding International Application No. PCT/US2021/024204 (16 pages).
Ceres, Midline Cervical Plate, Features and Benefits, Amendia (now Spinal Elements), MM-209, Rev. 0, believed to be publicly available at least as early as Mar. 25, 2020 (2 pages).
Ceres, Anterior Cervical Plate, Features and Benefits, Amendia (now Spinal Elements), MM-207, Rev. 0, believed to be publicly available at least as early as Mar. 25, 2020 (2 pages).
White Pearl, LIT-0008 Rev. C, Osseus, Dallas TX, believed to be publicly available at least as early as Mar. 25, 2020 (2 pages).
Blade, Anterior Cervical Plate System, Surgical Technique Guide 70-011, Rev. F, Nexxt Spine, Noblesville, IN, believed to be publicly available at least as early as Mar. 25, 2020 (12 pages).
Struxxure, Anterior Cervical Plate System, Surgical Technique Guide 70-024, Rev. F, Nexxt Spine, Noblesville, IN, believed to be publicly available at least as early as Mar. 25, 2020 (18 pages).

* cited by examiner

US 11,877,779 B2

BONE PLATE SYSTEM

CROSS-REFERENCE TO RELATED APPLICATION

This application claims the benefit of U.S. Provisional Patent Application No. 63/000,163, filed Mar. 26, 2020, which is hereby incorporated by reference in its entirety.

FIELD

This disclosure relates to bone plate systems and, more specifically, to bone plate systems having devices to limit back-out of bone screws of the bone plate systems.

BACKGROUND

Bone plate systems are often used to stabilize adjacent bones or portions of a bone. For convenience, the term "bone" as used herein is intended to encompass a bone or a portion of a bone. Bone plate systems often include a bone plate which is placed against the bones and bone screws that are driven into throughbores of the bone plate and into the bone to secure the bone plate to the bones. Bone plate systems often include devices to inhibit back-out of the bone screws to ensure the bone plate and bone screw construct remains secured with the bones. The devices also limit back-out of the bone screw to keep the bone screws from projecting outward from the bone plate and irritating surrounding tissues.

Bone plates are often used to stabilize vertebrae to address an injury, intervertebral disc replacement, or other situation. Some bone plate systems for the cervical region of the spine utilize a spring retainer in each throughbore of the bone plate that deflects out of the way of the bone screw to permit a bone screw to advance into the throughbore and returns to its initial position in the throughbore to inhibit back-out the bone screw. The spring retainer may be made of a wire that extends across an upper surface of the bone screw head to limit back-out once the bone screw head is seated in the throughbore. One issue with these spring retainers is that the wire material is very thin which may make it difficult for a surgeon to visually ascertain whether the retainer is positioned above the bone screw head to limit back-out.

Some bone plate systems have a multiple-stage bone screw installation process. In a first stage, a bone screw is driven into a throughbore. In a subsequent stage, the surgeon moves a rigid member into an overlapping position with the bone screw head to limit back-out of the bone screw. This multiple-stage process may complete installation of a bone plate system.

DETAILED DESCRIPTION

Figure 1:
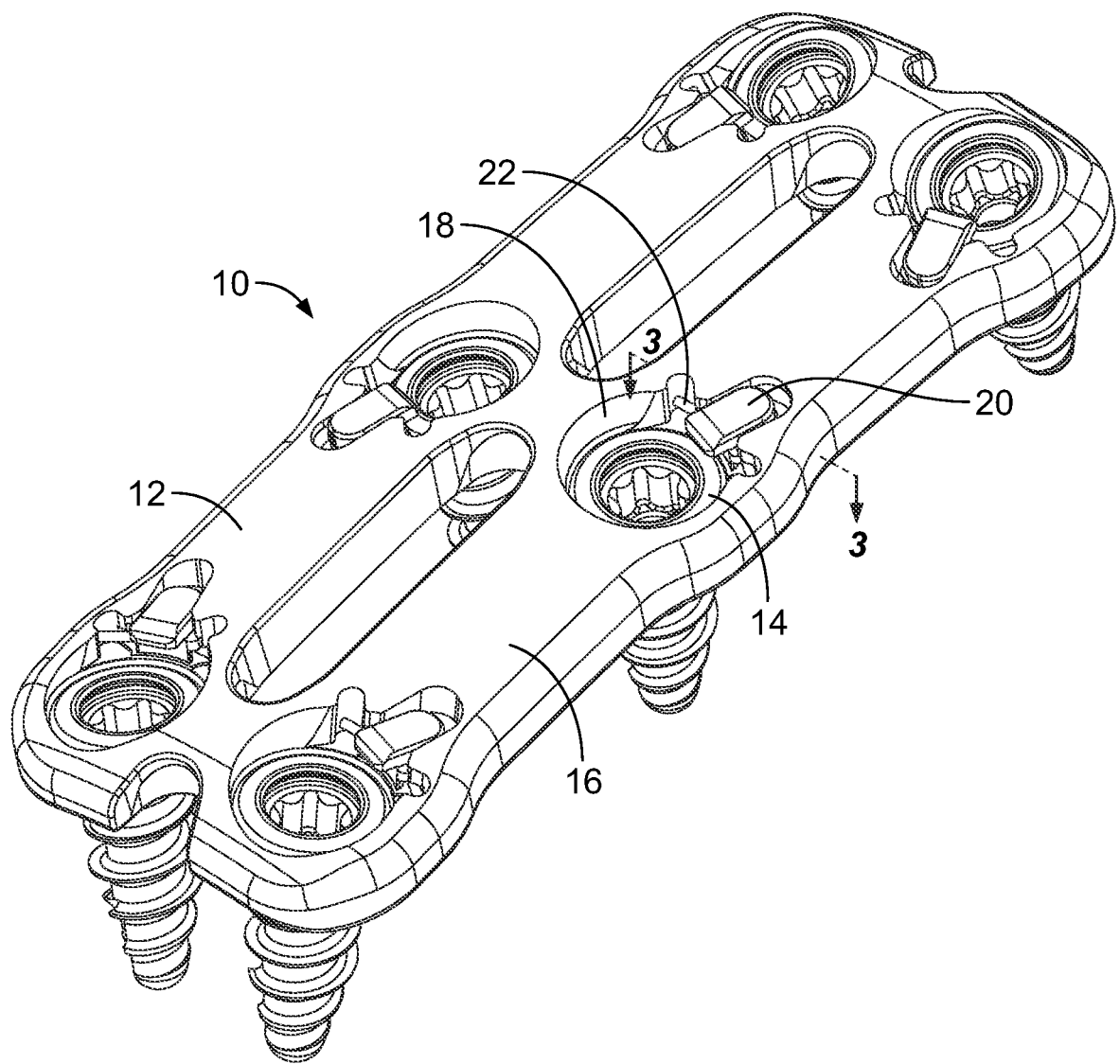
FIG. 1 is a perspective view of a bone plate system including a bone plate, bone screws, and sliders of the bone plate that inhibit back-out of the bone screws from throughbores of the bone plate.

Regarding FIG. 1, a bone plate system 10 is provided that includes a bone plate 12 and bone screws 14. The bone plate 12 includes a body 16 having throughbores 18 formed therein for receiving the bone screws 14. The throughbores 18 each have a central, longitudinal axis 19. The bone plate 12 includes retainers, such as one or more sliders 20, and resilient members, such as pins 22, urging the sliders 20 laterally to an interference position. The bone screws 14 each include a head portion 24 (see FIG. 16) having a tapered surface 260 configured to urge the respective slider 20 from the interference position to a clearance position and permit the head portion 24 to advance beyond the slider 20 and be seated in the throughbore 18. The pin 22 resiliently returns the slider 20 to the interference position above the bone screw head portion 24 to inhibit back-out of the bone screw 14 from the throughbore 18.

Figure 2:
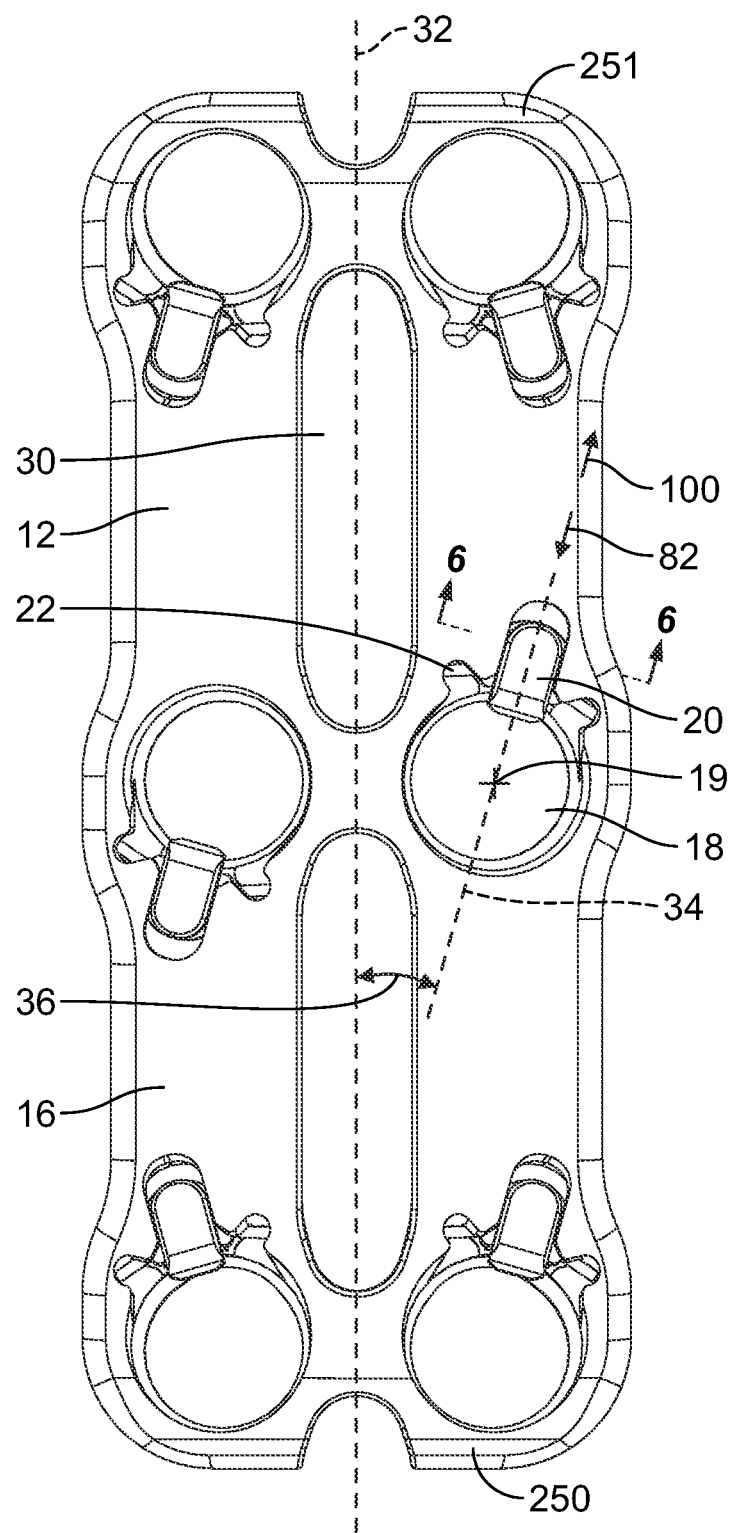
FIG. 2 is a top plan view of the bone plate of FIG. 1 showing the sliders of the throughbores in an interference position wherein the sliders extend into the throughbores to overlap head portions of the bone screws.
Figure 9:
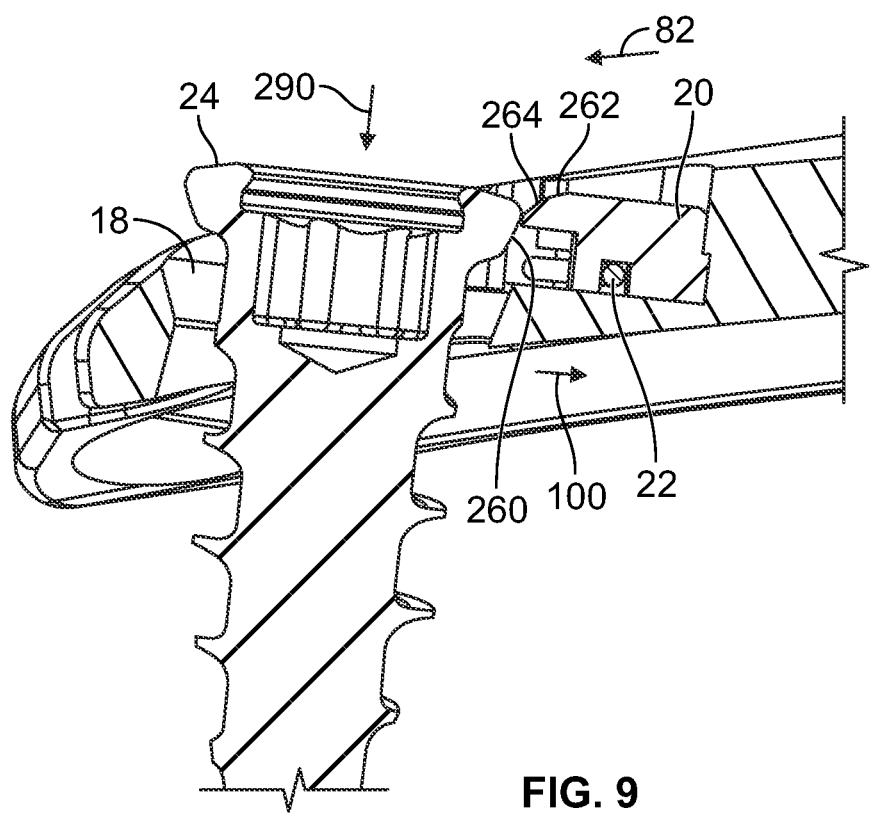
FIG. 9 is a cross-sectional view similar to FIG. 7 showing the bone screw advanced farther into the thorughbore and a side surface of the bone screw head portion keeping the slider in the clearance position thereof which permits the bone screw head portion to travel beyond the slider.

Regarding FIG. 2, the bone plate body 16 includes one or more windows 30 to permit bones or an implant therebetween to be observed by a surgeon. The bone plate body 16 may be elongated and have a longitudinal axis 32 and each slider 20 may be slidable along a path 34. In one embodiment, the path 34 is straight and extends at an angle 36 relative to the longitudinal axis 32. The one plate body 16 may include a receptacle for each slider 20 that includes an undercut 42 and an opening 48. The slider 20 may be constrained to sliding movement in the bone plate body 16 by way of a lower level 40 (see FIG. 6) received in the undercut 42 of the bone plate body 16. The slider 20 has a narrower, upper level 44 with an upper face 46 visible through the opening 48 in an upper surface 50 of the bone plate body 16. The opening 48 opens to the undercut 42 and permits the upper level 44 of the slider 20 to be visible whether the slider 20 is in the interference position (see FIG. 2) or the clearance position (see FIG. 9). In this manner, a surgeon may readily visually ascertain whether the slider 20 has been shifted back by the pin 22 to the interference position upon seating of the bone screw 14 in the throughbore 18. Further, the pin 22 snaps the slider 20 back to the interference position once the bone screw head portion 24 is advanced beyond the slider 20 which provide a tactile indication that the slider 20 has returned to the interference position.

Figure 3:
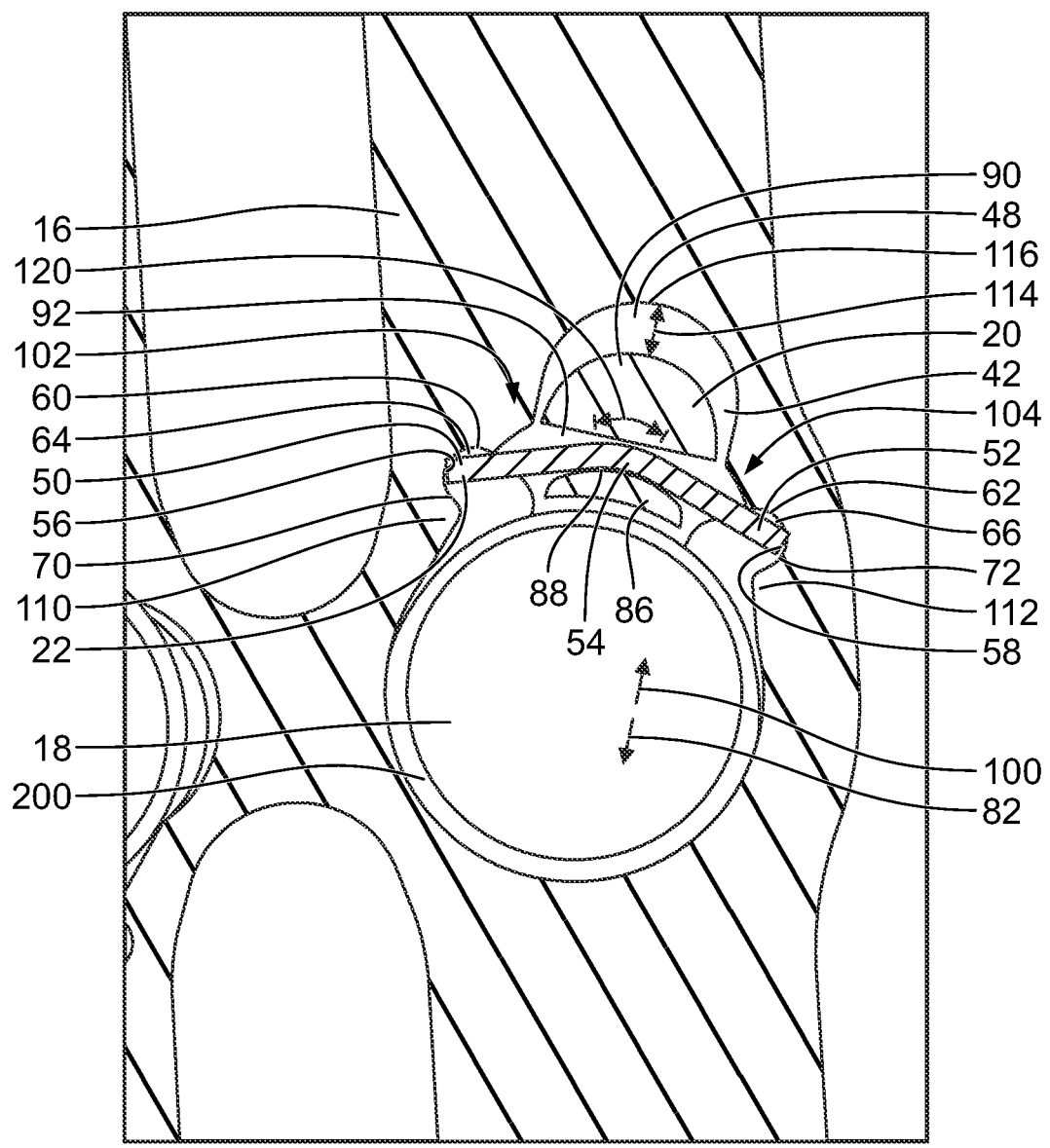
FIG. 3 is a cross-sectional view taken across line 3-3 in FIG. 1 showing a resilient pin of the bone plate in an initial configuration wherein ends of the pin are pressed against surfaces of pockets of the bone plate.
Figure 11:
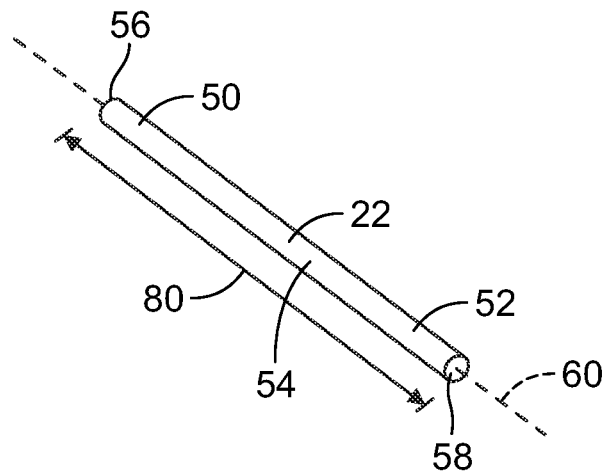
FIG. 11 is a perspective view of the resilient pin of FIG. 3 in an unloaded configuration.

Regarding FIGS. 2 and 3, the slider 20 is shown in the interference position. The pin 22 is under a preload with the pin 22 and slider 20 mounted to the bone plate body 16. Regarding momentarily to FIG. 11, the pin 22 has an underformed configuration wherein the pin 22 is straight. Returning to FIG. 3, the pin 22 has opposite end portions 50, 52, and an intermediate portion 54 therebetween. The pin 22 has ends 56, 58 and a longitudinal axis 59 (see FIG. 11) extending between the ends 56, 58. The pin 22 is loaded upon assembly of pin 22 and slider 20 with the bone plate body 16 as discussed in greater detail below. The pin 22 is bent when the slider 20 is in the interference position and is bent further with the slider 20 in the clearance portion. The pin may have a cross-section transverse to the length 80 that is uniform for at least a majority of the length 80. The cross-section may be, for example, circular or rectangular.

Regarding FIG. 3, the bone plate body 16 has pockets 60, 62 that include recesses 64, 66 which open to the undercut 42. The pockets 60, 62 include surfaces 70, 72 against which the ends 56, 58 are tightly engaged by the preloaded pin 22. The pin 22 is biased to straighten out to its unloaded configuration (see FIG. 11); however, the distance between the surfaces 70, 72 is less than the length 80 of the pin 22 in the unloaded configuration. In other words, the pocket 60, 62 are too close together to permit the pin 22 to straighten out. The engagement between the ends 56, 58 of the pin 22 and the surfaces 70, 72 of pockets 60, 62 inhibits the pin 22 from shifting radially inward in direction 82.

The slider 20 has a bending member, such as a wall 86 having a curved surface 88 configured to contact the intermediate portion 54 of the pin 22. As shown in FIG. 3, the slider 20 is in the initial, interference position wherein the intermediate portion 54 of the pin contacts the wall 86 to bias the slider 20 toward the interference position. The slider 20 further includes a foot portion 90 spaced from the wall 86 to form a channel 92 therebetween. The pin 22 extends in the channel 92 with the end portions 50, 52 of the pin projecting laterally outward from the slider 20 and into the pockets 60, 62. The wall 86 supports the intermediate portion 54 of the pin 22 as a fulcrum about which the pin 22 may bend with shifting of the slider 20 in direction 100 toward the clearance position thereof.

Regarding FIG. 3, the bone plate body 16 includes supports 102, 104 on opposite sides of the slider 20 configured to support the end portions 50, 52 and provide a base for the end portions 50, 52 to contact and urge the slider 20 back toward the interference position. Opposite the supports 102, 104, the bone plate body 16 includes retainer portions 110, 112 that are spaced apart a distance smaller than the length 80 of the pin 22 to inhibit the pin 22 from straightening out and exiting the bone plate body 16.

With the slider 20 in the interference position, the foot portion 90 of the slider 20 is spaced a distance 114 from a wall 116 of the bone plate body 16. Further, the intermediate portion 54 of the pin 22 is in contact with the curved surface 88 a length 120. The curved surface 88 provides a gradual transition for the pin 22 that limits stress risers in the pin 22.

Figure 4:
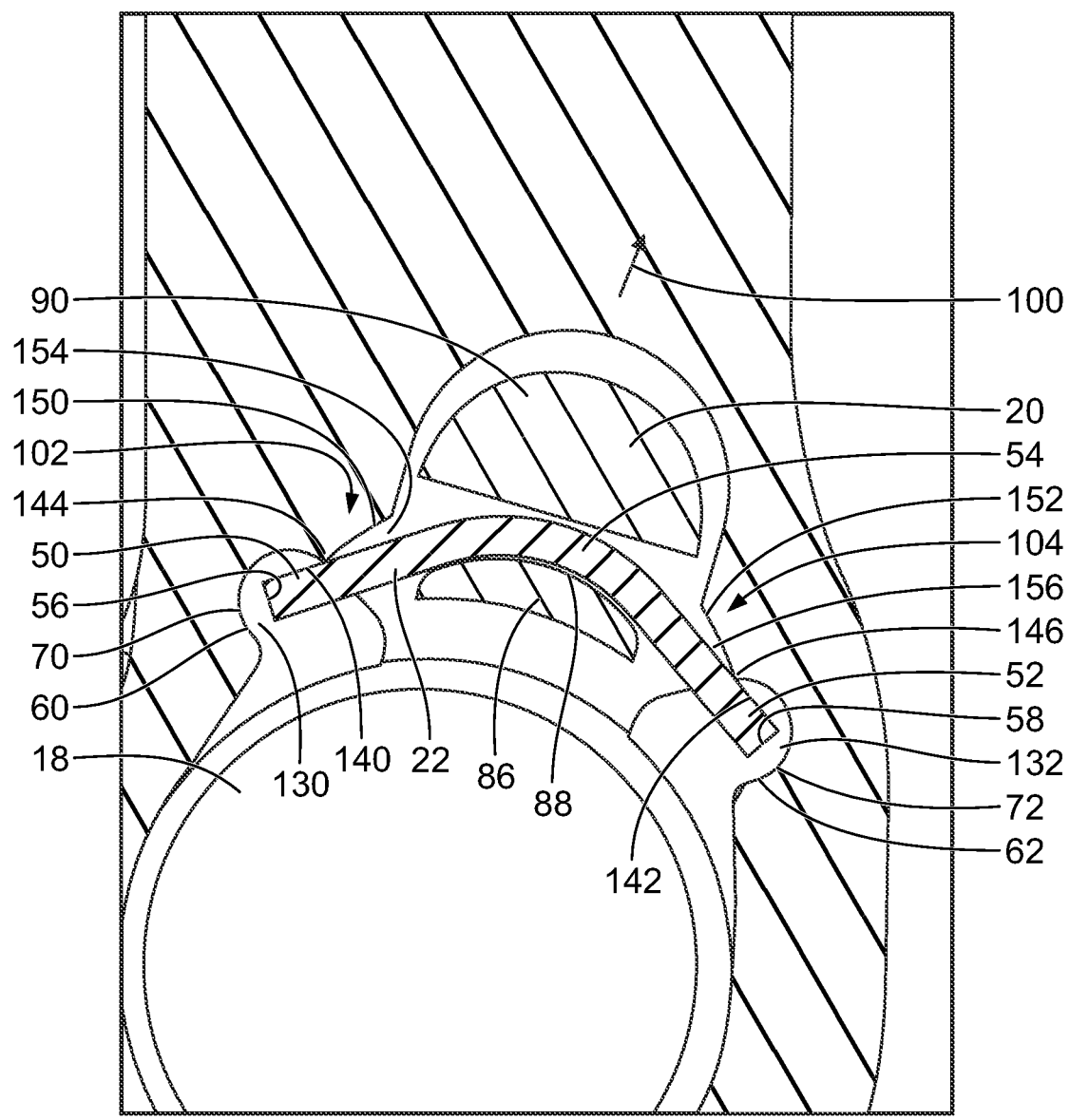
FIG. 4 is a cross-sectional view similar to FIG. 3 showing the slider having been shifted radially outward which shifts the end portions of the pin out of contact with the pocket surfaces of the bone plate.

Regarding FIG. 4, the slider 20 has been shifted in radial or lateral outward direction 100 by a bone screw head portion (not shown in FIG. 4) as the bone screw head portion is being advanced into the throughbore 18. The shifting of the slider 20 in direction 100 causes the wall 86 and curved surface 88 thereof to press against a center portion, such as the intermediate portion 54, of the pin 22. The wall 86 shifts the intermediate portion 54 in direction 100 with the slider 20 and shifts the ends 56, 58 of the pin 22 away from the surfaces 70, 72 of the pockets 60, 62. This forms gaps 130, 132 between the ends 56, 58 and the surfaces 70, 72. With the slider 20 in this intermediate position, the ends 56, 58 of the pin 22 are no longer pressed against the surfaces 70, 72. Further, the end portions 50, 52 have opposite side portions, such as outer side surface portions 140, 142, contacting portions of the support 102, 104 such as edges 144, 146. The intermediate portion 54 of the pin 22 is bent more in the intermediate position of FIG. 4 than with the slider 20 in the interference position of FIG. 3. Further, the end portions 50, 52 are closer together when the slider 20 is in the intermediate position than when the slider 20 is in the interference position. As shown in FIG. 4, the supports 102, 104 include support surfaces 150, 152 that are spaced from the end portions 50, 52 of the pin 22 by gaps 154, 156 when the slider 20 is in the intermediate position.

Figure 5:
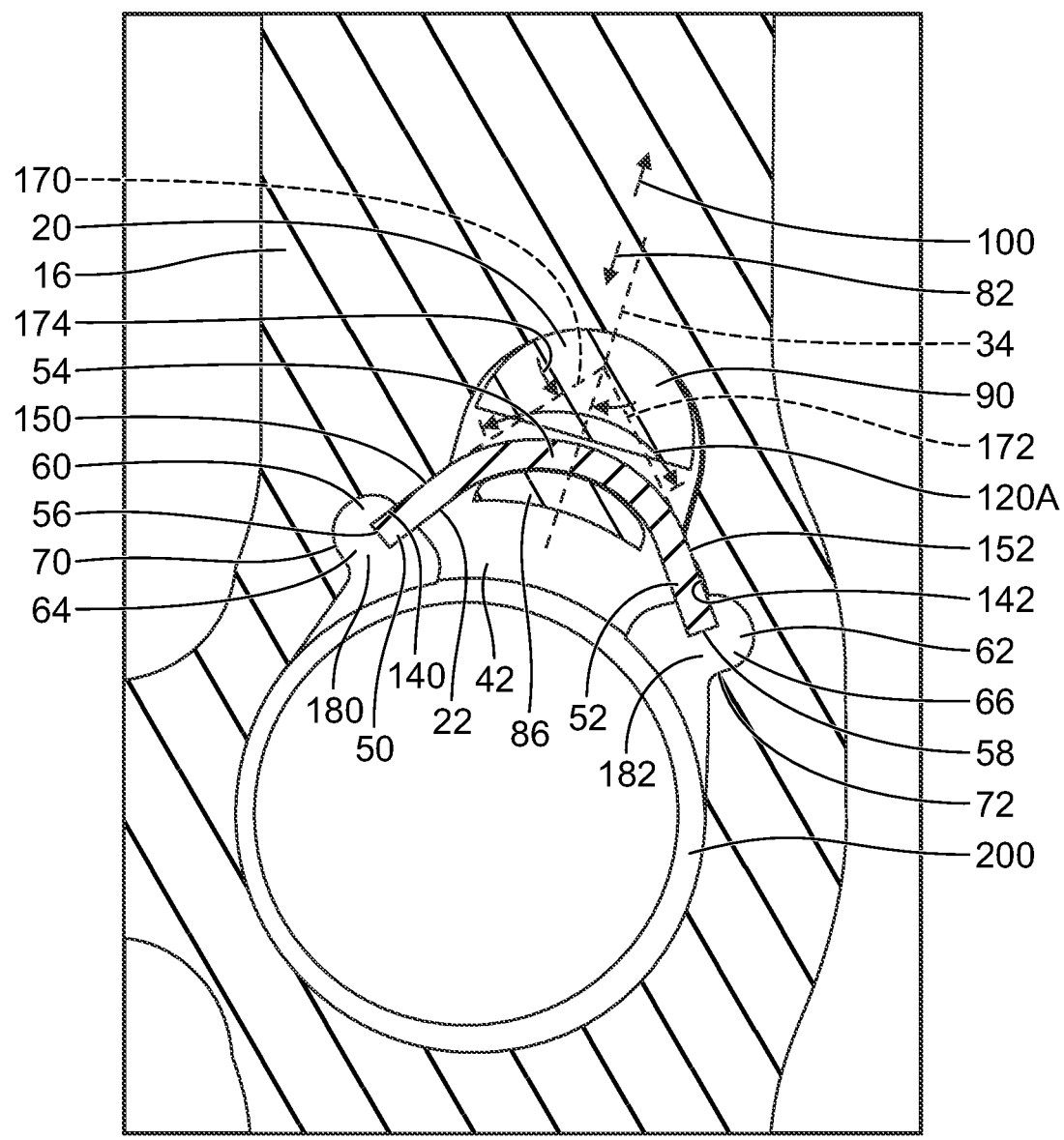
FIG. 5 is a cross-sectional view similar to FIG. 3 showing the slider in a clearance position wherein a bone screw may be driven into the throughbore and seated therein.

Regarding FIG. 5, the bone screw head portion has shifted to the slider 20 radially outward in direction 100 to the clearance position thereof. This causes the wall surface 88 of the slider 20 to further shift the intermediate portion 54 away from the throughbore 18 so that the pin 22 extends a length 120A along the wall surface 88 that is greater than the length 120 as shown in FIG. 3. The support surfaces 150, 152 of the bone plate body 16 may be curved to compliment the curving of the pin 22 caused by the shifting of the slider 20 to the clearance position. The support surfaces 150, 152 may generally extend along axes 170, 172 that are each oriented at an angle 174 relative to the path 34 of the slider 20. As shown in FIG. 5, the ends 56, 58 of the pin 22 are spaced from the pocket surfaces 70, 72 by larger gaps 180, 182 than in the intermediate position of the slider 20 shown in FIG.

4. The ends 56, 58 have at least been partially withdrawn from the recesses 64, 66 of the pockets 60, 62 when the slider 20 is in the clearance position.

As shown in FIG. 5, the pin 22 generally has three points of contact including the support surface 150, the support surface 152, and the surface 88. The pin 22 is resiliently deformed in this configuration and is biased to straighten out and urge the slider 20 back radially inward in direction 82 toward the interference position once the bone head portion 24 has seated against a seating surface 200 of the bone plate body 16. Once the bone head portion 24 is seated against the seating surface 200, the pin 22 straightens out which causes the intermediate portion 54 to urge the wall 86 of the slider 20 back laterally inward in direction 82 and permits the end portions 50, 52 of the pin 22 to snap back into the pockets 60, 62 and press against the surfaces 70, 72.

Figure 6:
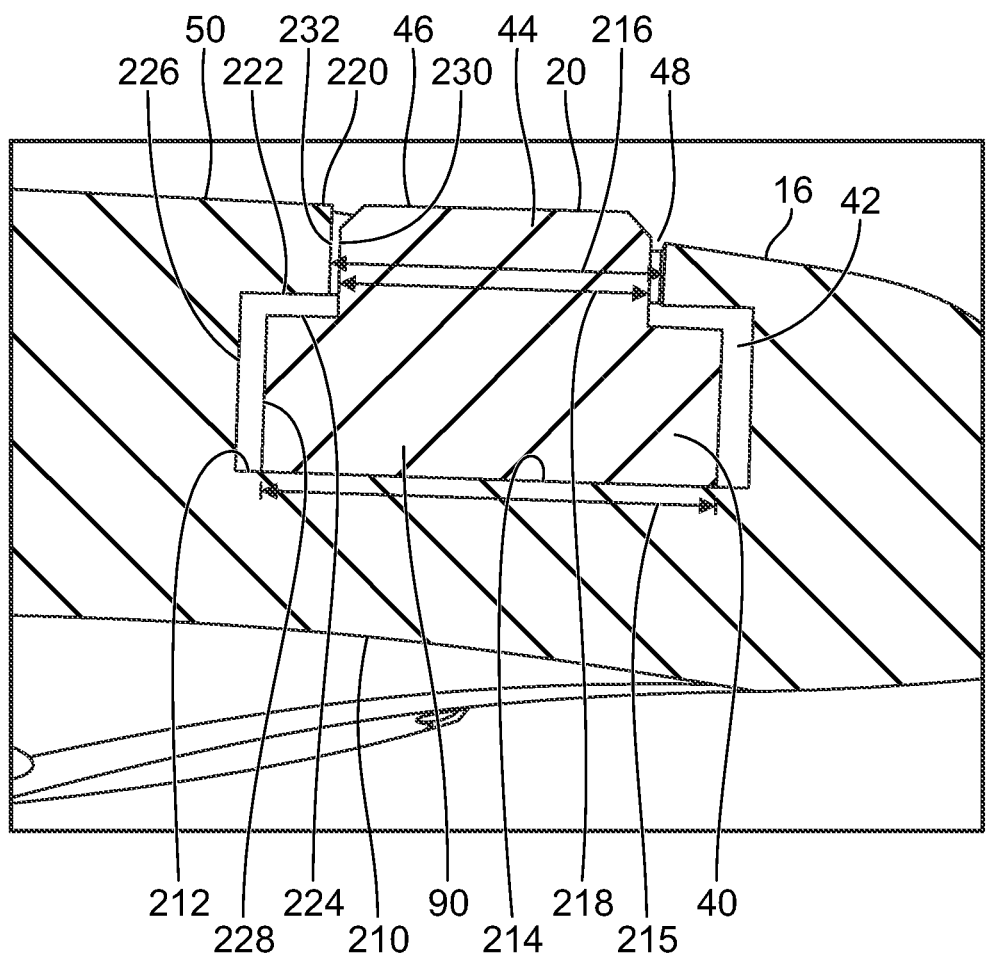
FIG. 6 is a cross-sectional view taken across line 6-6 in FIG. 2 showing a wider lower portion of the slider received in an undercut of the bone plate.

Regarding FIG. 6, the bone plate body 16 has a lower surface 210 opposite the upper surface 50. The undercut 42 includes a floor 212 that supports a bottom face 214 of the lower level 40 of the slider 20. The lower level 40 has a width 215 that is wider than a width 216 of the opening 48 and a width 218 of the upper level 44 of the slider 20. The bone plate body 16 includes overhangs, such as upper walls 220, that at least in part define the opening 48 and have lower surfaces 222 facing upper faces 224 of the lower level 40. The bone plate body 16 further includes lower side walls 226 facing side wall portions 228 of the lower level 40. At the upper level 44, the slider 20 includes upper side wall portions 230 that face upper side walls 232 of the upper walls 220. In this manner, the sliders 20 have notched profiles on the opposite sides thereof and the bone plate body 16 has narrow sections that extend into the notched profiles and form an example of a slide connection between the bone plate body 16 and the slider 20.

Figure 7:
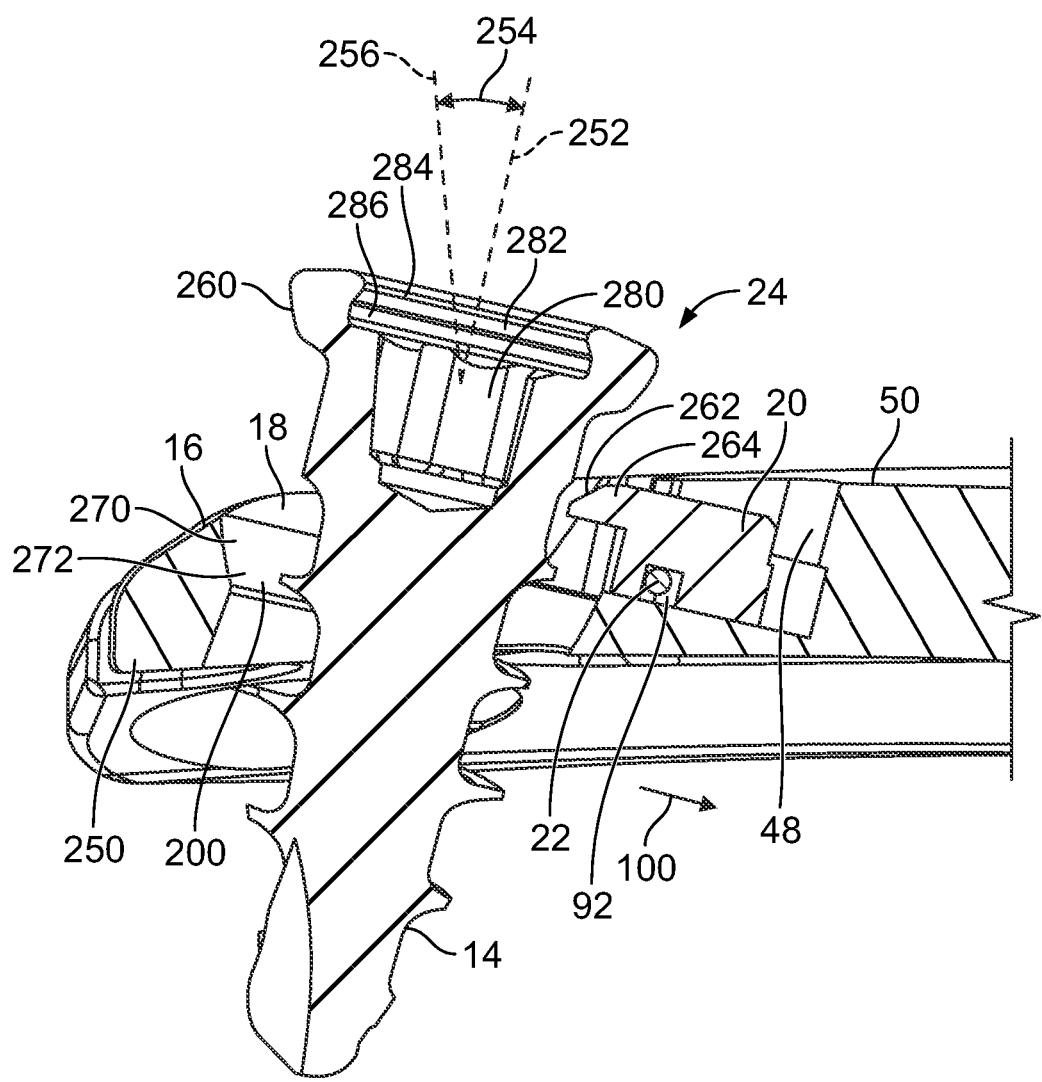
FIG. 7 is a cross-sectional view of the bone plate taken across line 7-7 in FIG. 2 in combination with a bone screw being driven into a throughbore and the slider in the interference position thereof.

Regarding FIG. 7, a throughbore 18 at an end portion 250 of the bone plate body 16 is shown. The throughbore 18 has a central, longitudinal bore axis 252 that may be at an angle 254 from an axis 256 generally normal to the upper surface 250 of the bone plate body 16. The throughbore 18 may be configured to permit the surgeon to toe out the bone screws 14 in the throughbores 18 at the end portions 250, 251 of the bone plate body 16. The head portion 24 of the bone screw 14 includes a tapered surface 260 that performs multiple functions. One function is to engage a tapered surface 262 of a lip portion 264 of the slider 20 and cammingly shift the slider 20 in lateral or radial direction 100 as the bone head portion 24 is advanced into the throughbore 18. Another function of the surface 260 is to seat against the seating surface 200 of the bone plate body 16. The seating surface 200 may be generally concave, including an upper portion 270 having an inner diameter and a lower portion 272 having a smaller inner diameter. The seating surface 200 permits polyaxial insertion of the bone screw 14 into the throughbore 18. Further, the surfaces 200, 260 may be configured to permit controlled pivoting of the bone screw 14 relative to the bone plate body 16 such as due to subsidence of the bones to which the bone plate 12 is secured.

The head portion 24 of the bone screw 14 includes a rotary drive structure 280 for receiving a driving tool. The head portion 24 may include an opening 282 that opens to the rotary drive structure 280, a collar portion 284, and an undercut 286. The driver may have a portion that extends into the undercut 286 to retain the bone screw 14 on the driver tool as the driver tool is used to advance the bone screw 14 into the throughbore 18. The rotary drive structure 280 may have a Torx configuration as one example.

Figure 8:
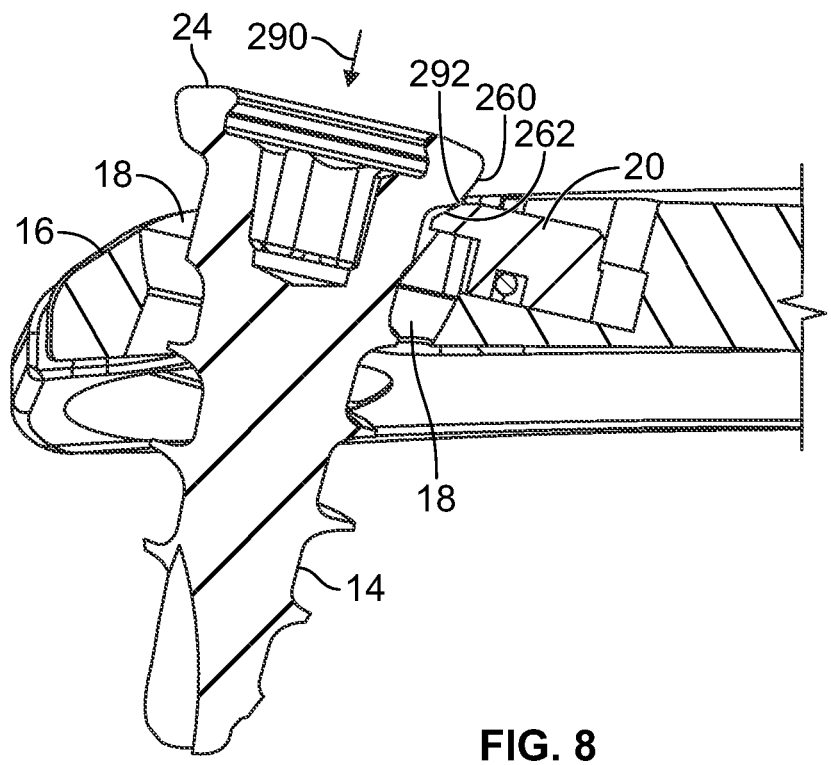
FIG. 8 is a cross-sectional view similar to FIG. 7 showing a lower surface of a head portion of the bone screw contacting a tapered surface of the slider and beginning to shift the slider radially outward.
Figure 10:
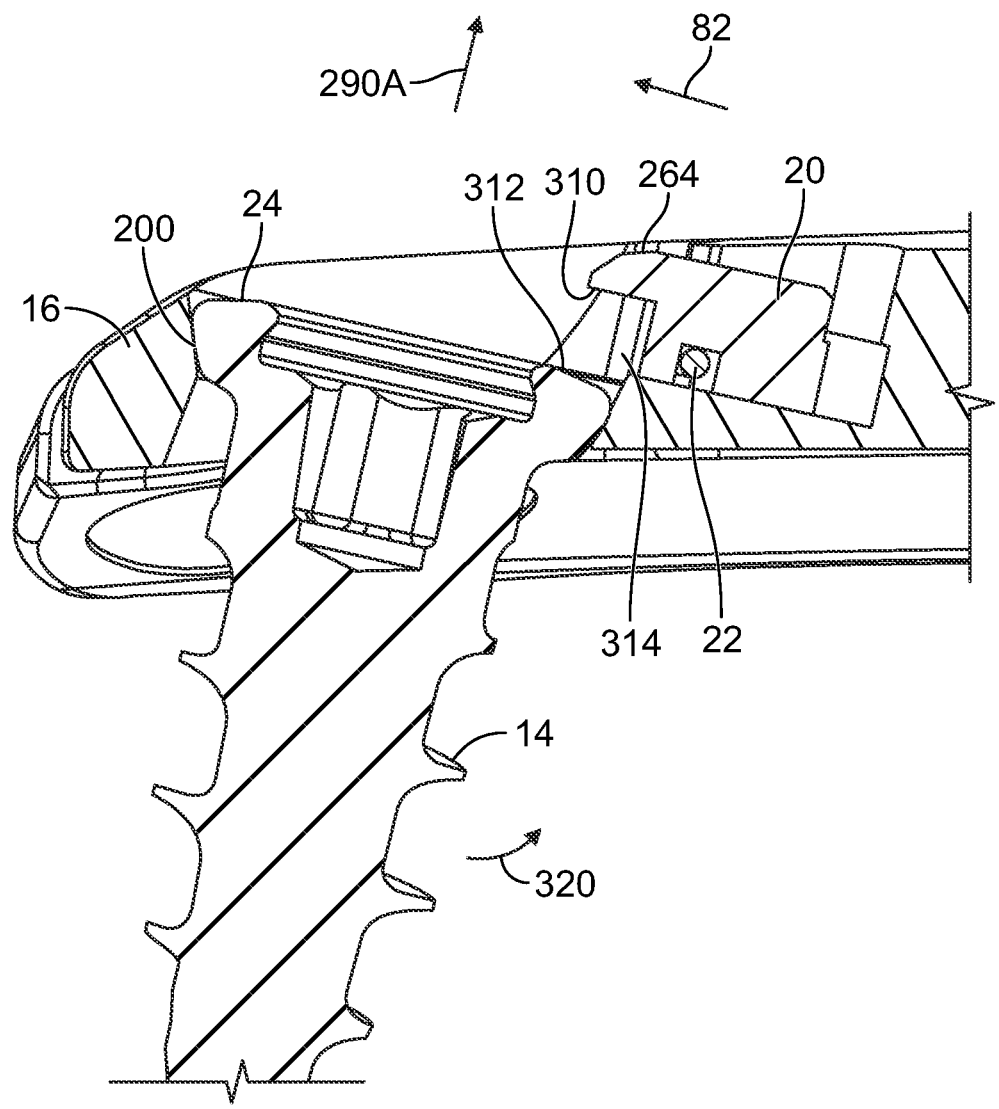
FIG. 10 is a cross-sectional view similar to FIG. 7 showing the bone screw head portion seated in the throughbore and the slider having shifted radially inward to the interference position wherein a lip portion of the slider is positioned above the bone screw head portion to inhibit back-out of the bone screw from the throughbore.

Regarding FIG. 8, the bone screw 14 is shown and driven in direction 290 into the throughbore 18 with a lower edge 292 of the bone screw head portion 24 contacting the tapered surface 262 of the slider 20. Regarding FIG. 9, continued advancing of the bone screw 14 in direction 290 brings the tapered surface 260 of the bone screw head portion 24 into camming engagement with the tapered surface 262 of the slider 20 such that the camming engagement between surfaces 260, 262 shifts the slider 20 outward laterally in direction 100 to the clearance position thereof so that the head portion 24 may be advanced into the throughbore 18. As the head portion 24 is advanced in direction 290, the pin 22 is deflected and biases the slider 20 back toward the interference position in direction 82. Regarding FIG. 10, the head portion 24 of the bone screw 14 shown seated against the seating surface 200 of the bone plate body 16. The pin 22 has urged the slider 20 in direction 82 back to the interference position. The slider 20 has the lip portion 264 thereof with a lower surface 310 overlapping upper surface 312 of the bone screw head portion 24. Thus, the lower surface 310 of the slider 20 is positioned to contact the upper surface 312 and inhibit back-out of the bone screw 14 in direction 290A. The lip portion 264 of the slider 20 provides a gap 314 between the lower surface 310 and the upper surface 312. The gap 314 permits controlled pivoting or angulation of the bone screw 14. Specifically, the gap 314 permits the bone screw 14 to turn in direction 320 with subsidence of the bones stabilized by the bone plate system 10.

Figure 12:
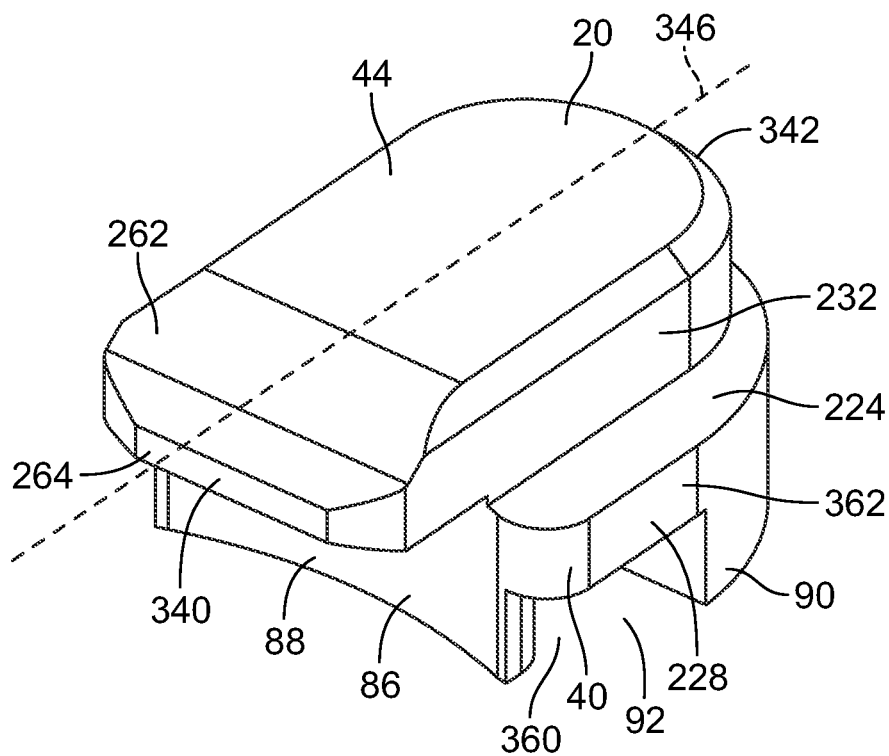
FIG. 12 is a perspective view of one of the sliders of the bone plate of FIG. 1 showing a channel for receiving the resilient pin.
Figure 14:
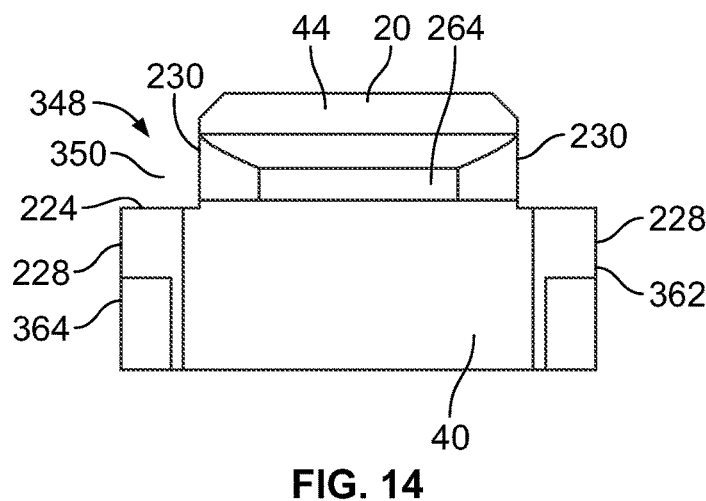
FIG. 14 is a front elevational view of the slider of FIG. 12 showing the step profile of the sides of the slider.

Regarding FIGS. 12 and 14, the slider 20 has an inboard end 340, an outboard end 342, and an axis 346 extending therebetween. The narrower upper level 44 forms a step profile 348 with a notch 350 on opposite sides of the slider 20 for receiving the upper walls of the bone plate body 16. The upper side wall portions 230 may be parallel to the lower side wall portions 228 and the upper face 224 of the lower level 40 extends therebetween.

Figure 13:
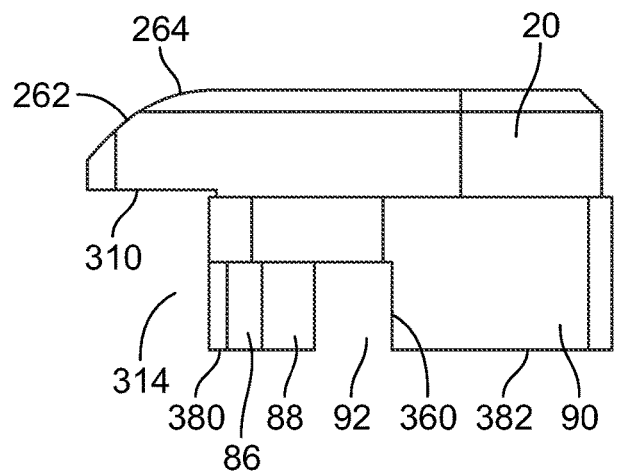
FIG. 13 is a side elevational view of the slider of FIG. 12 showing a foot portion and a wall of the slider on opposite sides of the channel.

Regarding FIGS. 12 and 13, the slider 20 includes a through opening for receiving the pin 22 such as the channel 92. The channel 92 may include a flared portion 360 at sides 362, 364 of the slider 20. The flared portions 360 provide clearance for the intermediate portion 54 of the pin 22 to deflect as the slider 20 is moved between the clearance and interference positions.

Figure 15:
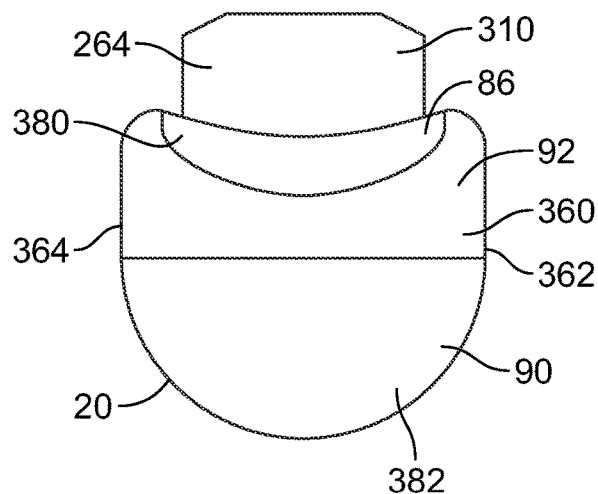
FIG. 15 is a bottom plan view of the slider of FIG. 12 showing a curved profile of the wall that bends an intermediate portion of the resilient pin.

Regarding FIGS. 13 and 15, the wall 86 and the foot portion 90 of the slider 20 include lower surfaces 380, 382 configured to slide along a floor surface 212 (see FIG. 6) of the bone plate body 16. The surfaces 380, 382 and 212 may be flat or have other shapes, e.g. protrusions, or textures.

Figure 16:
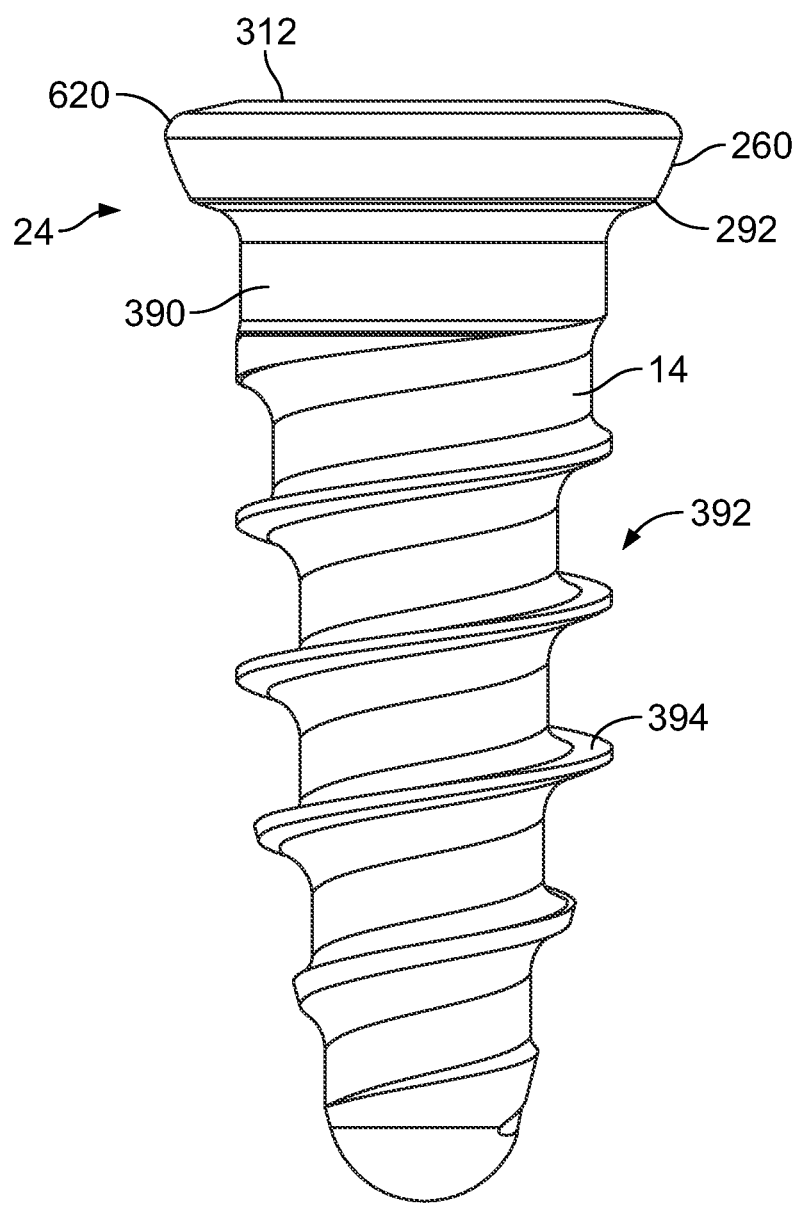
FIG. 16 is a side elevational view of one of the bone screws of FIG. 1.
Figure 17:
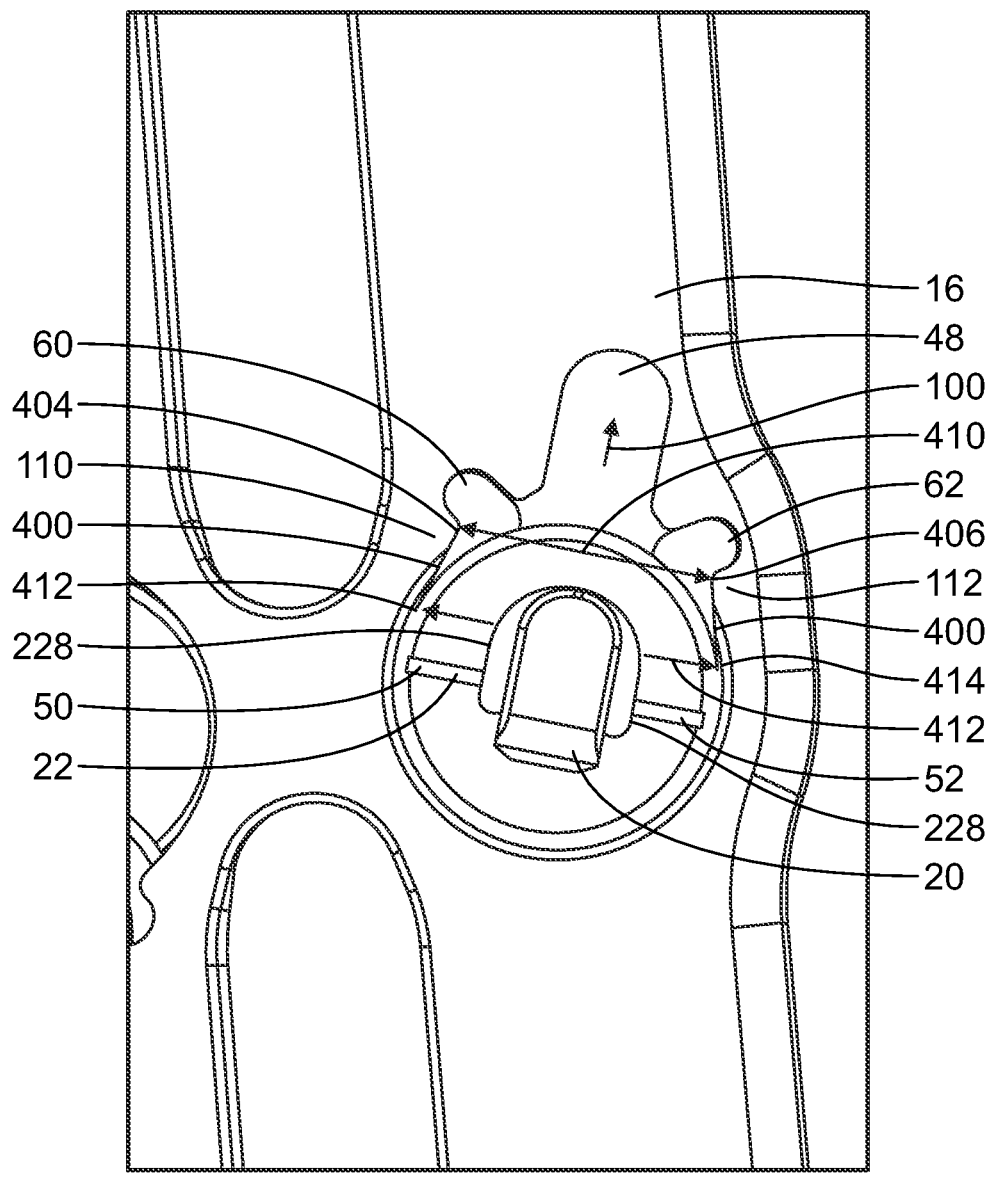
FIGS. 17, 18, 19 and 20 are top plan views of a throughbore of the bone plate of FIG. 1 showing an example process for assembling the slider and pin in the bone plate body.

Regarding FIG. 16, the bone screw 14 includes the head portion 24 having a cylindrical surface 390. The bone screw 14 further includes a shank portion 392 depending from the head portion 24 that may include threads 394. Threads 394 may be single lead or multiple lead threads as some examples.

Regarding FIGS. 17-20, a method of assembling the slider 20, pin 22, and the bone plate body 16 is shown. Regarding FIG. 17, the slider 20 is positioned in the throughbore 18 with the pin 22 in a straight, undeflected configuration extending in the channel 92. The end portions 50, 52 of the pin 22 extend outward from the side wall portions 228 of the slider 20. The retainer portions 110, 112 of the bone plate body 16 include tapered guide surfaces 400, 402 that are inclined and extend toward each other as the surfaces 400, 402 extend away from the throughbore 18 and end at edges 404, 406. The edges 404, 406 are separated by a width or distance 410 that is less than a distance 412 of the widest portions 412, 414 of the tapered guide surfaces 400, 402. The distance 410 may be less than a maximum width of the pin 22 such as the length 80.

Figure 18:
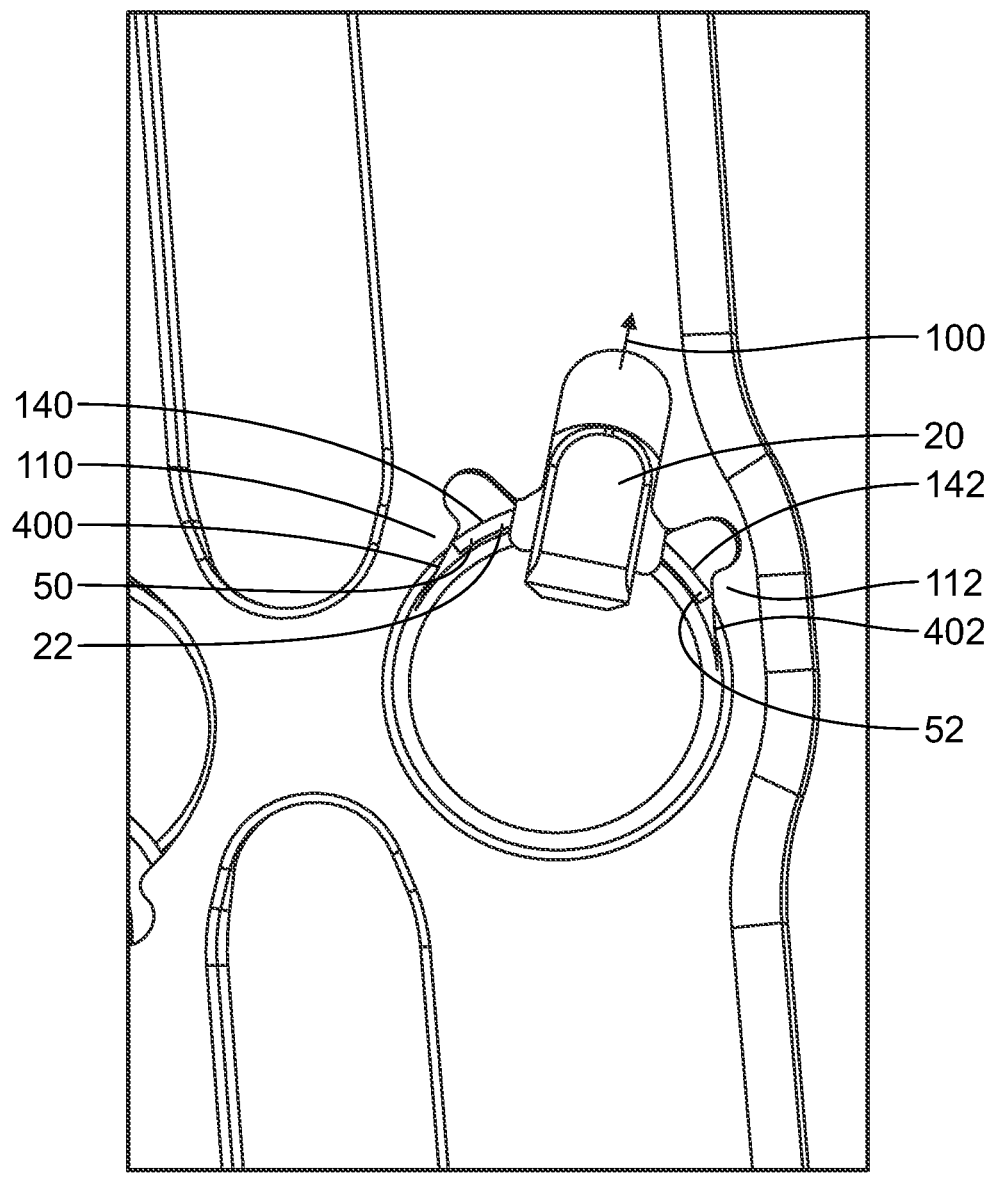

Regarding FIG. 18, the slider 20 has been shifted in direction 100 such that the outer side surface portions 140, 142 of the pin 22 slide along the tapered guide surfaces 400, 402. Because the length 80 of the pin 22 in the undeflected configuration is larger than the distance 410, shifting the slider 20 in direction 100 causes the pin 22 to bend as the intermediate portion 54 of the pin 22 is bent and moves with the slider 20 while the end portions 50, 52 are engaging and sliding along the tapered guide surfaces 400, 402. The tapered guide surfaces 400, 402 cause the end portions 50, 52 to be urged together as the slider 20 shifts in direction 100.

Figure 19:
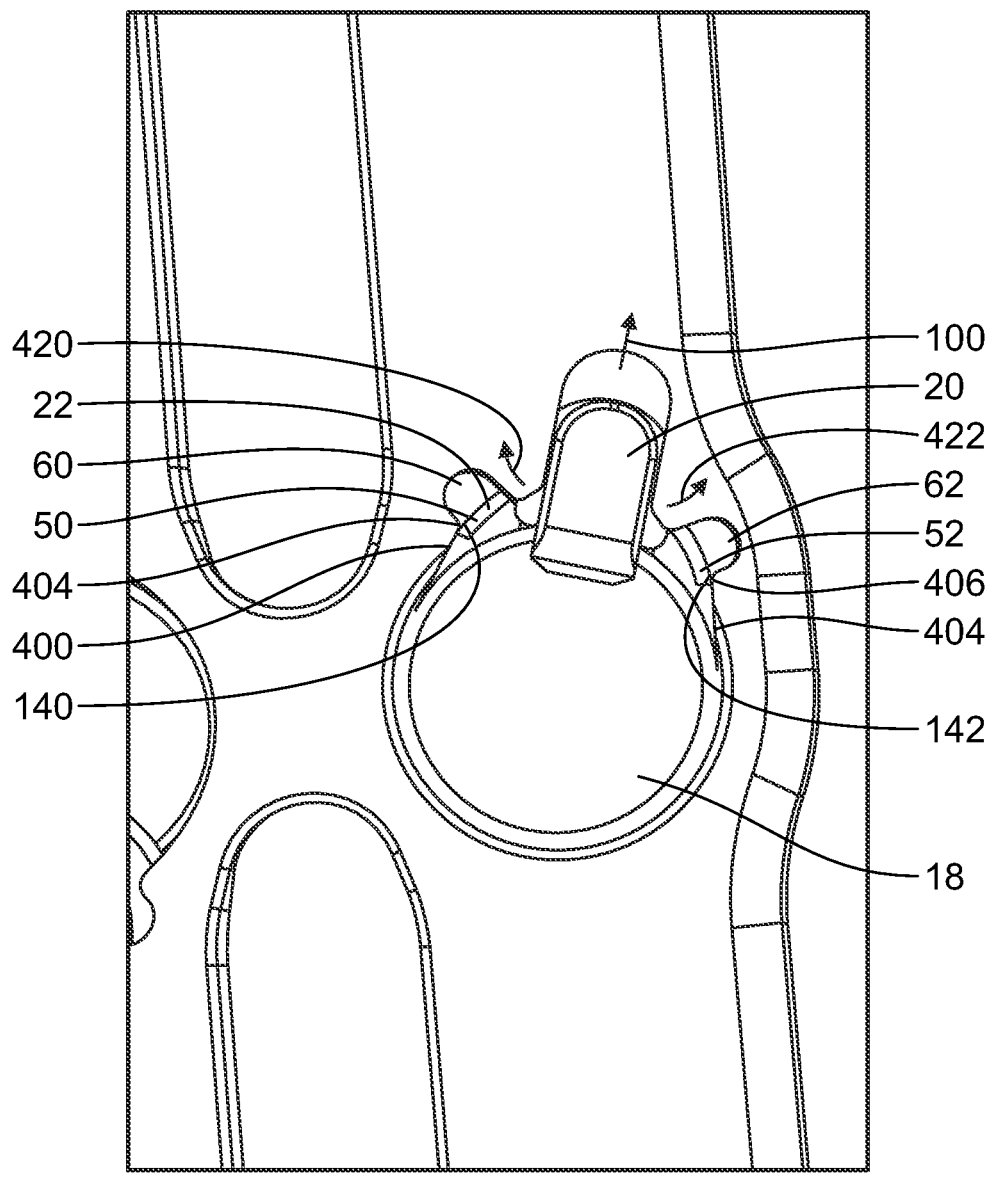
Figure 20:
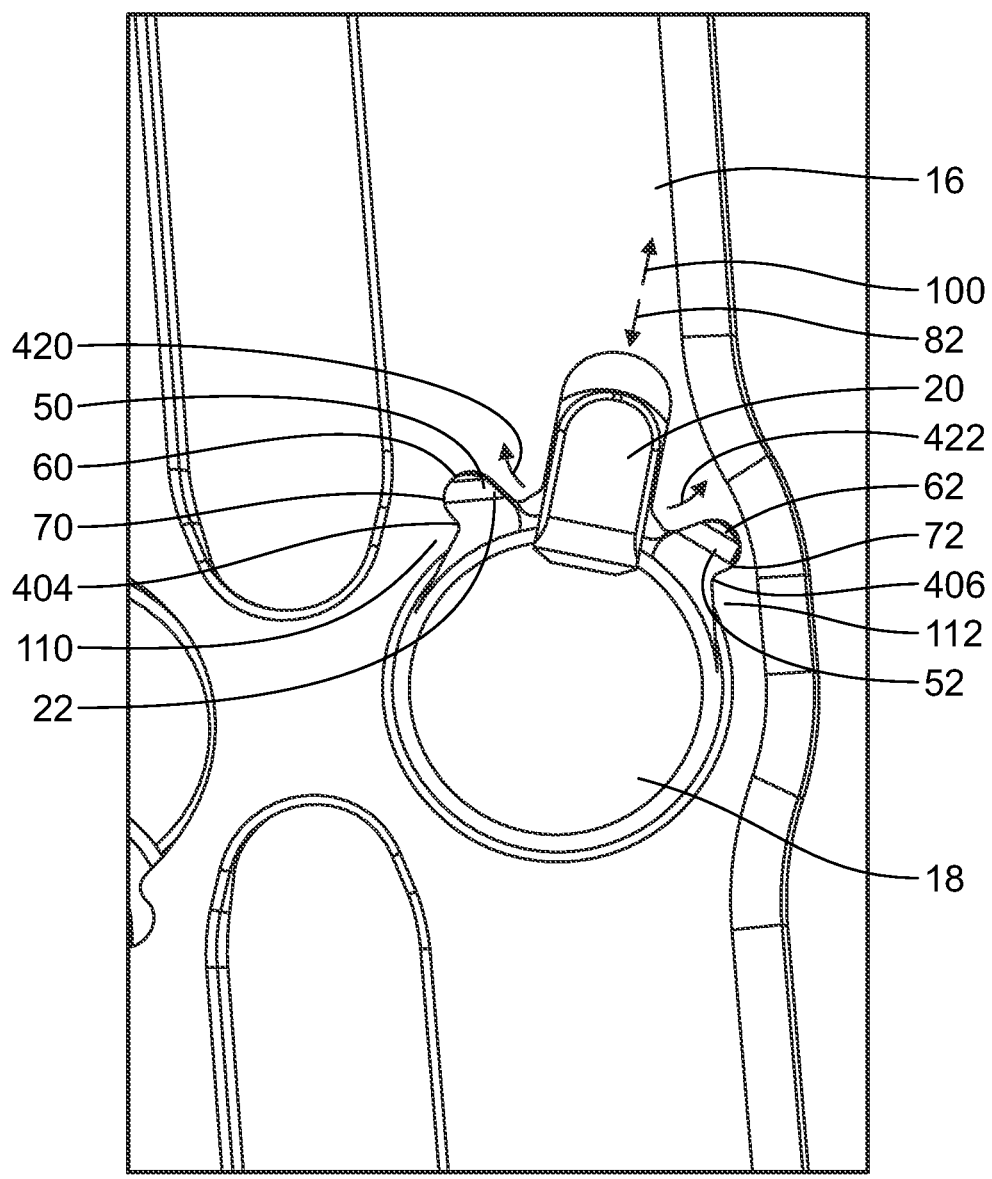

Regarding FIG. 19, the slider 20 is continued to be shifted in direction 100 and the outer side surface portions 140, 142 of the pin 22 are engaged with the edges 404, 406 of the bone plate body 16. The pin 22 is bent and is resiliently urging the end portions 50, 52 apart in directions 420, 422. Regarding FIG. 20, the slider 20 has been shifted in direction 100 to a position where the end portions 50, 52 of the pin 22 have shifted radially beyond edges 404, 406 such that the end portions 50, 52 may snap apart and into the pockets 60, 62. Once the end portions 50, 52 have snapped into the pockets 60, 62, the slider 20 may be released and the pin 22 urges the end portions 50, 52 in directions 420, 422 against the surfaces 70, 72 of the pockets 60, 62. As noted above, the edges 404, 406 are separated by the distance 410 which is less than the length 80 of the unloaded pin 22 such that the retainer portions 110, 112 of the bone plate inhibit the pin 22 from fully unloading and urging the slider in direction 100A. In this manner, the pin 22 may be assembled with the slider 20 and the bone plate body 16 and the preload applied to the pin 22. The preload in the pin 22 keeps the pin 22 in a bent configuration in the bone plate body 16 so that the pin 22 resists movement of the slider 20 in direction 82A and positions the pin 22 to be shifted with the slider 20 in direction 100 upon the advancing of the bone screw into the throughbore 18.

Figure 21:
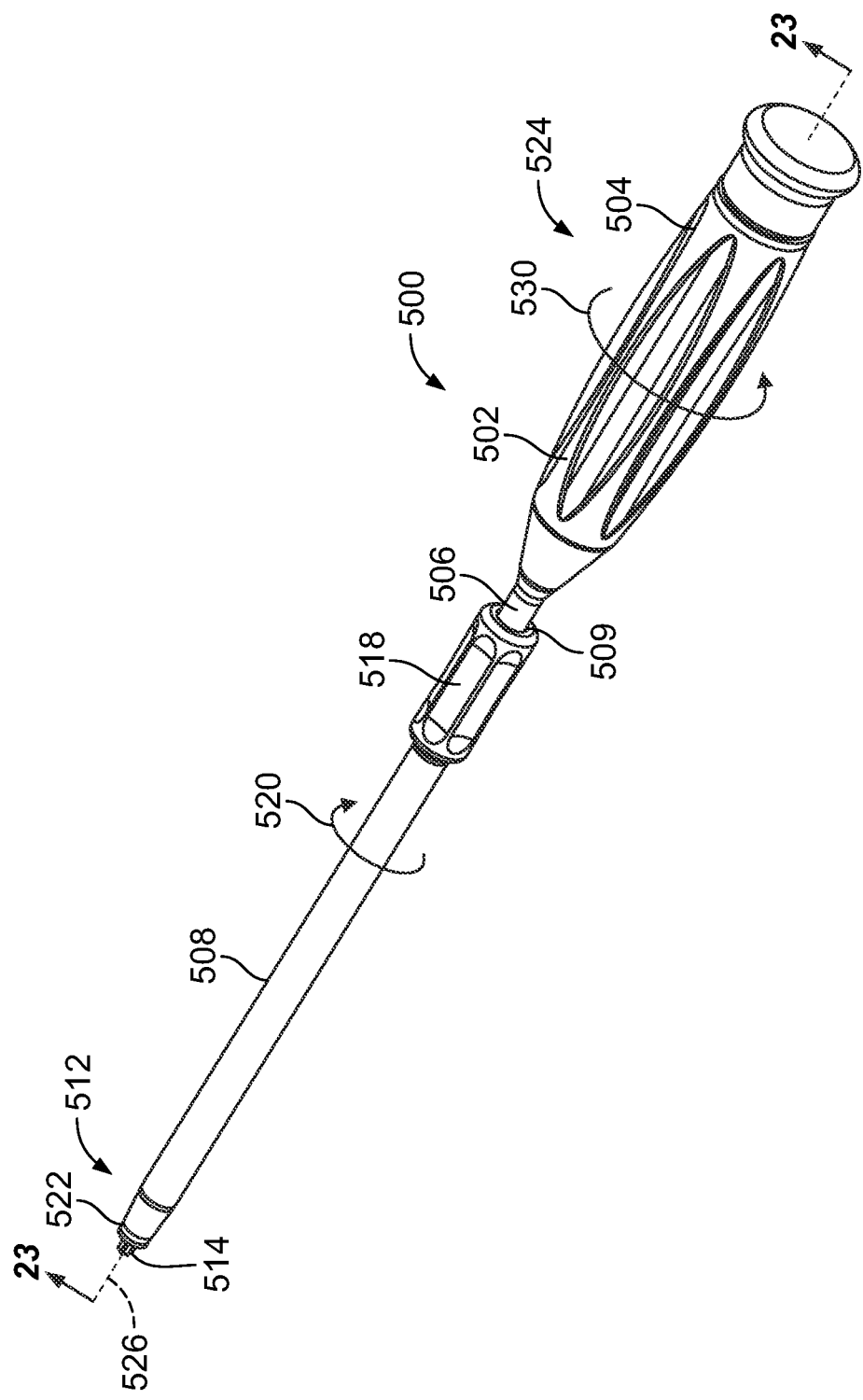
FIG. 21 is a perspective view of a bone screw removal tool for removing a bone screw from a bone plate system of FIG. 1.

Regarding FIG. 21, a bone screw remover tool 500 is provided that permits a surgeon to connect the bone screw remover tool 500 to a bone screw 14 in a throughbore 18, shift the slider 20 out of the way of the bone screw 14, and then turn the bone screw 14 to remove the bone screw 14 from the throughbore 18. More specifically, the bone screw remover tool 500 includes a driver 502 having a handle 504 and a shaft 506. The bone screw remover tool 500 has a sleeve 508 with a cannula 509 through which the shaft 506 extends until protruding at a driving member, such as a driving tip 514 having a rotary drive structure 516 (see FIG. 22). The sleeve 508 has a knob 518 and is rotatably connected to the shaft 506 of the driver 502. In this manner, the surgeon may turn the knob 518 in direction 520 to cause the sleeve 508 and a cam portion 522 thereof to shift the slider 20 from the interference position to the clearance position and then may turn the handle 504 and driving tip 514 connected thereto to remove the associated bone screw 14. As shown in FIG. 21, the bone screw remover tool 500 has a distal end portion 512 and a proximal end portion 524, and a longitudinal axis 526 extending therebetween. As noted above, the sleeve 508 may be rotated relative to the driver 502 in direction 520. Conversely, the driver 502 may be rotated in direction 530 relative to the sleeve 508 to loosen the bone screw 14 while the sleeve 508 keeps the slider 20 in the clearance position thereof. In some embodiments, a surgeon may connect the driving tip 514 to a bone screw 14, turn the sleeve 508 in direction 530 to shift the slider 20 to the clearance position, and then turn the driver 502 in direction 530 to remove the bone screw 14 from the throughbore 18.

Figure 22:
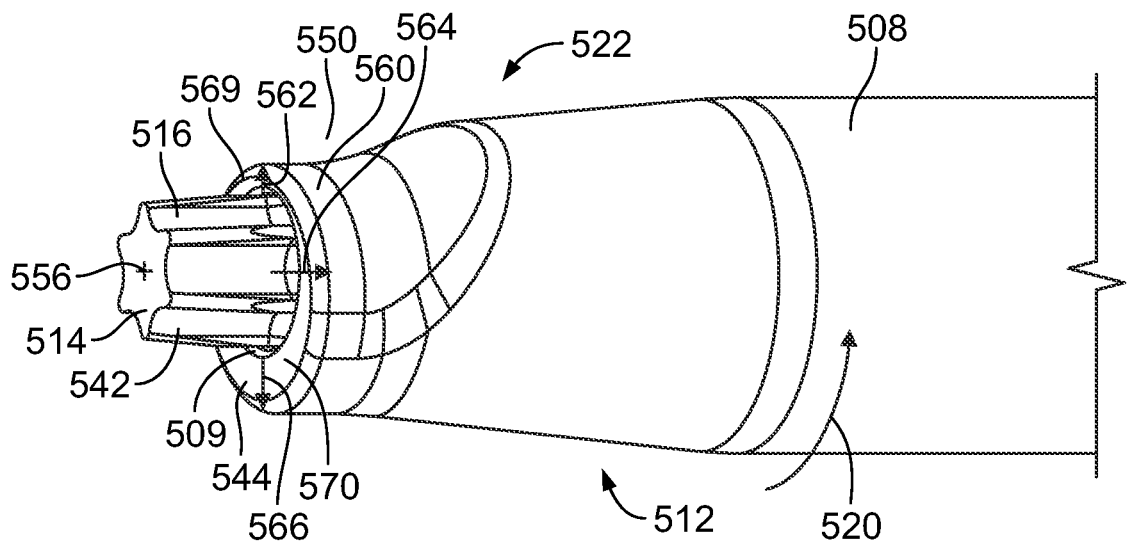
FIG. 22 is a perspective view of a distal end of the bone screw remover tool of FIG. 21 showing a driving tip of the tool.

Regarding FIG. 22, the driving tip 514 extends out from the cannula 509 of the sleeve 508 to expose the rotary drive structure 516, such as projections that fit into recesses of the rotary drive structure 280 of the bone screw 14. The rotary drive structure 516 may be, for example, a Torx driver. The driving tip 514 extends out of a distal surface 544 of the sleeve 508. The surface 544 may be adapted to seat against the upper surface 312 (see FIG. 24) of the bone screw head portion 24. The cam portion 522 of the sleeve 508 has a recess 550 that is axially aligned with the slider 20 before the driving tip 514 is advanced into the throughbore 18. The recess 550 provides clearance for the sleeve 508 to be advanced without contacting the lip portion 264 of the slider 20. The surface 544 may have a general circular periphery with a center that is eccentric to a center 556 of the driving tip 514. The cam portion 522 includes a cam surface 560 having radii 562, 564, 566 from the center 556 of the driving tip 514 that increase as the cam surface 560 extends clockwise (in FIG. 22) about the driving tip 514 from the approximate twelve o'clock position to the proximate six o'clock position. Once the driving tip 514 has been advanced into engagement with the rotary drive structure 280 of the bone screw head portion 24, the surgeon may turn the sleeve 508 in direction 520 about the shaft 506 to cause a radially enlarged portion 570 of the sleeve 508 to rotate into contact with the slider 20 and shift the slider 20 in direction 100 from the interference position to the clearance position.

Figure 23:
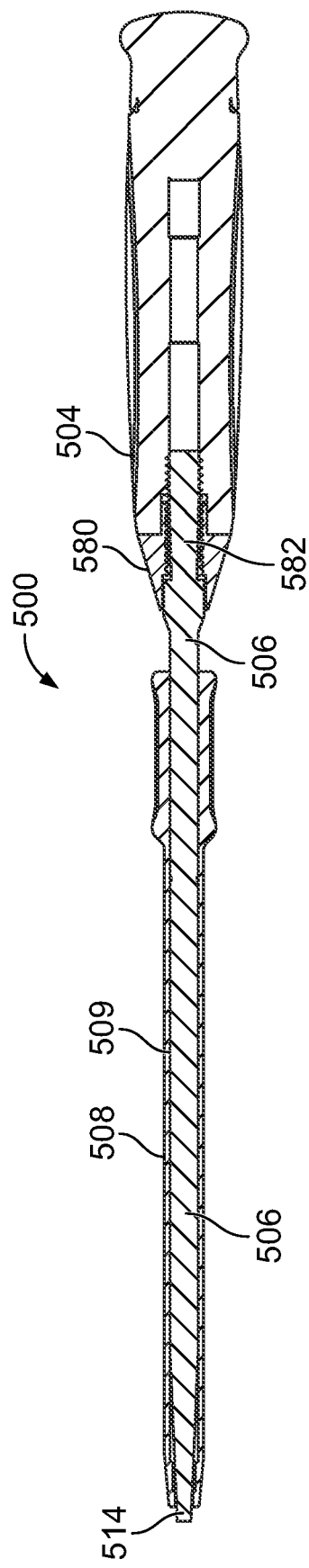
FIG. 23 is a cross-sectional view taken across line 23-23 in FIG. 21 showing an internal shaft of the tool extending through a sleeve of the tool.

Regarding FIG. 23, a cross section of the bone screw remover tool 500 is provided. The handle 504 may be secured using adhesive, welds, or fastener(s) to a collar 580. The collar 580 may be threadingly engaged with a threaded portion 582 of the shaft 506. The shaft 506 extends through the cannula 509 of the sleeve 508 to project outward of the driving tip 514.

Figure 24:
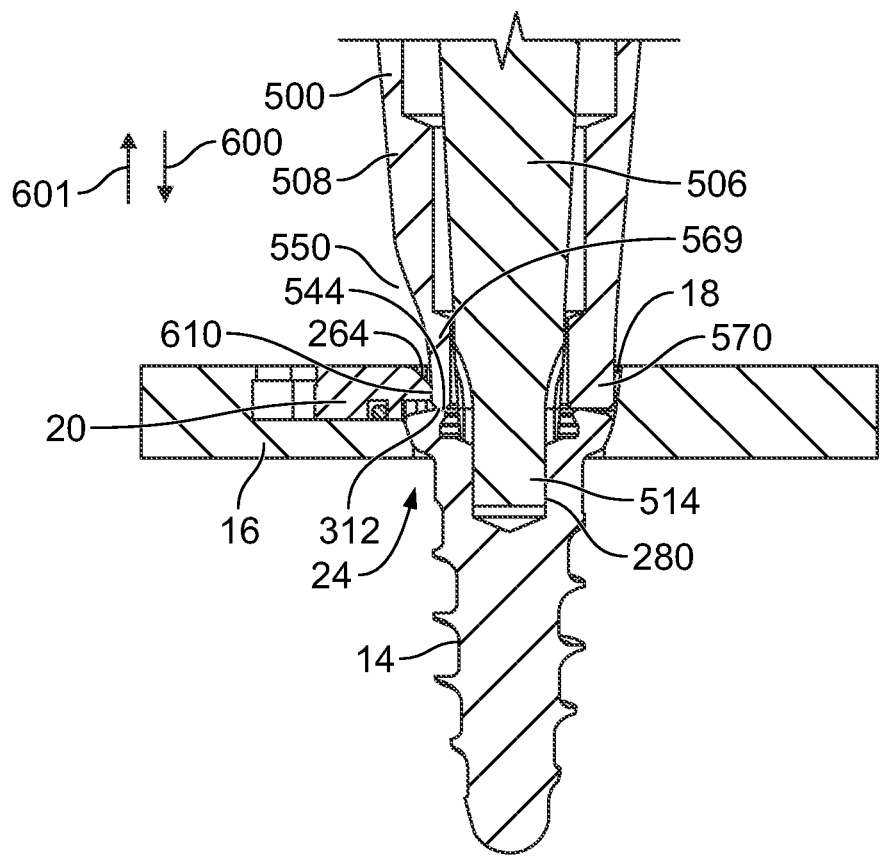
FIG. 24 is a cross-sectional view of a distal end of the bone screw remover tool showing the sleeve positioned to shift the slider radially outward with turning of the sleeve.

Regarding FIG. 24, the bone screw remover tool 500 has been connected to the bone screw 14 by aligning the recess 550 of the sleeve 508 with the slider 20 and advancing the driving tip 514 in direction 600 into the rotary drive structure 280 of the bone screw head portion 24. A radially narrow portion 569 of the sleeve 508 is positioned radially intermediate the slider 20 and the shaft 506. Next, the surgeon turns the sleeve 508 around the shaft 506 and cammingly engage the cam surface 560 of the sleeve 508 with the surface 610 of the slider 20 to shift the slider 20 from the interference position to the clearance position. The surgeon turns the sleeve 508 in direction 520 until the radially enlarged portion 570 of the sleeve 508 is radially intermediate the slider 20 and the shaft 506. The presence of the thicker, radially enlarged portion 570 against the slider 20 keeps the slider 20 in the clearance position. With the slider 20 in the clearance position, the surgeon may turn the handle 504 in direction 530 which causes the corresponding turning of the driving tip 514 in direction 530 and removes the bone screw 14 from the bone and the throughbore 518. The radially enlarged portion 570 of the sleeve 508 is sized to have an outer radius that is similar to a maximum outer radius of the bone screw head portion 24, such as a corner 620 (see FIG. 16), so that the radially enlarged portion 570 of the sleeve 508 may hold the slider 20 in the clearance position as the head portion 24 is removed in direction 601 until the slider 20 can transition into contact with the tapered surface 260 of the bone screw head portion 24. The slider 20 may slide along the tapered surface 26 as the bone screw head portion 24 is removed from the throughbore 18.

Uses of singular terms such as "a," "an," are intended to cover both the singular and the plural, unless otherwise indicated herein or clearly contradicted by context. The terms "comprising," "having," "including," and "containing" are to be construed as open-ended terms. It is intended that the phrase "at least one of" as used herein be interpreted in the disjunctive sense. For example, the phrase "at least one of A and B" is intended to encompass A, B, or both A and B.

While there have been illustrated and described particular embodiments of the present invention, it will be appreciated that numerous changes and modifications will occur to those skilled in the art, and it is intended for the present invention to cover all those changes and modifications which fall within the scope of the appended claims.

What is claimed is:

1. A bone plate system comprising:
    a bone plate body including a throughbore;
    a bone screw having a head portion with a rotary drive structure and a threaded shank portion, the threaded shank portion configured to be advanced into the throughbore and driven into bone;
    a slider slidably connected to the bone plate body to slide between a clearance position wherein the slider permits the bone screw head portion to be advanced into the throughbore and seated against the bone plate body and an interference position wherein the slider inhibits bone screw back out from the throughbore with the bone screw head portion seated against the bone plate body in the throughbore;
    an elongate, resilient pin distinct from the slider, the resilient pin being bent and having a preload with the slider in the interference position such that the resilient pin engages the bone plate body with the slider in the interference position;
    the slider having a surface configured to contact and further bend an intermediate portion of the resilient pin which further loads the resilient pin as the bone screw head portion shifts the slider from the interference position toward the clearance position in a first direction, the resilient pin configured to unload and urge the slider from the clearance position toward the interference position in a second direction opposite the first direction upon the bone screw head portion seating against the bone plate body in the throughbore; and
    the resilient pin resists shifting of the slider in the second direction beyond the interference position to keep the slider in the interference position with the bone screw head portion seated against the bone plate body in the throughbore.

2. The bone plate system of claim 1 wherein the resilient pin includes opposite end portions, the opposite end portions engaged with the bone plate body and the intermediate portion contacting the surface of the slider in the clearance position thereof to urge the slider toward the interference position.

3. The bone plate system of claim 1 wherein the connection between the slider and the bone plate body limits the slider to shifting along an axis between the clearance and interference positions; and
    the bone plate body includes a pair of support surfaces on opposite sides of the axis and extending transverse thereto, the pair of support surfaces of the bone plate body configured to contact end portions of the resilient pin with the slider in the clearance position and support the resilient pin as the resilient pin urges the slider toward the interference position.

4. The bone plate system of claim 1 wherein the slider shifts an entirety of the resilient pin relative to the bone plate body with shifting of the slider between the clearance and interference positions thereof.

5. The bone plate system of claim 1 wherein the resilient pin has an unloaded configuration wherein the resilient pin is straight.

6. The bone plate system of claim 1 wherein the resilient pin has ends that are closer together with the slider in the clearance position than with the slider in the interference position.

7. The bone plate system of claim 1 wherein the resilient pin is captured between the slider and the bone plate body.

8. The bone plate system of claim 1 wherein the slider includes a channel comprising the surface; and
    wherein the resilient pin extends in the channel of the slider.

9. The bone plate system of claim 1 wherein the resilient pin includes opposite end portions, the surface of the slider having a curvature to support the intermediate portion of the resilient pin.

10. The bone plate system of claim 1 wherein the bone plate body includes recesses on opposite sides of the slider, the resilient pin having end portions received in different ones of the recesses.

11. The bone plate system of claim 1 wherein the bone screw head portion includes an upper annular surface and the slider includes a lip portion configured to extend radially over the upper annular surface with the slider in the interference position and the bone screw head portion seated against the bone plate body in the throughbore.

12. The bone plate system of claim 1 wherein the bone plate body includes a lower surface configured to be positioned against a bone and an upper surface opposite the lower surface;
    wherein the bone plate body includes an undercut in communication with the throughbore and an upper opening in the upper surface that opens to the undercut; and
    the slider includes a lower portion in the undercut and an upper portion in the upper opening of the bone plate body, the slider upper portion being visible from above the bone plate body with the slider in the interference and clearance positions.

13. The bone plate system of claim 1 wherein the resilient pin is of a nitinol material.

14. The bone plate system of claim 1 wherein the resilient pin has a length and a uniform cross section perpendicular to the length throughout a majority of the length of the resilient pin.

15. The bone plate system of claim 1 wherein the slider includes a bending member having the surface thereon and a foot portion spaced from the bending member, the resilient pin intermediate the bending member and the foot portion; and
    wherein the bending member and the foot portion have lower surfaces configured to slide on a floor surface of the bone plate body.

16. The bone plate system of claim 1 wherein the bone plate body has surfaces on opposite sides of the slider;
    wherein the resilient pin has opposite end surfaces and a cylindrical side surface extending between the opposite end surfaces, the opposite end surfaces of the resilient pin being engaged with the surfaces on the opposite sides of the slider with the slider in the interference position; and wherein the opposite end surfaces of the resilient pin are spaced from the surfaces on the opposite sides of the slider with the slider in the clearance position.

17. A bone plate system comprising:
a bone plate body having an upper surface and a lower surface;
a throughbore of the bone plate body extending between the upper and lower surfaces of the bone plate body along a central, longitudinal axis of the throughbore;
a bone screw having a head portion and a threaded shank portion, the threaded shank portion configured to be advanced into the throughbore and driven into bone;
a slider slidably connected to the bone plate body to contact the bone screw as the bone screw is advanced into the throughbore, the slider configured to be slid along a path by the bone screw from a laterally inward, interference position wherein the slider inhibits bone screw back out from the throughbore to a laterally outward, clearance position wherein the slider permits the bone screw head portion to be advanced into the throughbore and seated against the bone plate body;
supports of the bone plate body on opposite sides of the slider and having a minimum width therebetween transverse to the path of the slider;
a resilient member assembled with the slider and having a maximum dimension when unloaded that is greater than the minimum width between the supports of the bone plate body;
the slider configured to deflect a center portion of the resilient member between the supports of the bone plate body and along the path of the slider as the bone screw contacts the slider and shifts the slider from the laterally inward, interference position to the laterally outward, clearance position;
side portions of the resilient member on opposite sides of the center portion configured to contact the supports of the bone plate body with the slider in the laterally outward, clearance position and urge the slider toward the laterally inward, interference position upon the bone screw head portion seating against the bone plate body;
wherein the bone plate body includes a recess adjacent each of the supports and the resilient member side portions extend into respective ones of the recesses with the slider in the interference position; and
wherein the supports include support surfaces on the opposite sides of the slider, each support surface including a first surface portion spaced by a gap from one of the resilient member side portions with the slider in the interference position, the first surface portion contacting the respective one resilient member side portion with the slider in the clearance position.

18. The bone plate system of claim 17 wherein the side portions of the resilient member include side surfaces configured to slide along the supports of the bone plate body as the slider slides from the interference position toward the clearance position.

19. The bone plate system of claim 17 wherein the resilient member side portions are at least partially withdrawn from the recesses with the slider in the clearance position.

20. The bone plate system of claim 16 wherein the support surfaces taper toward one another as the support surfaces extend laterally away from the throughbore.

21. The bone plate system of claim 17 wherein the support surfaces are curved.

22. The bone plate system of claim 17 wherein each support includes an edge configured to contact one of the resilient member side portions with the slider in the interference position and the support surface of the respective support is adjacent the edge.

23. The bone plate system of claim 17 wherein the slider includes a curved surface configured to contact the center portion of the resilient member.

24. The bone plate system of claim 17 wherein the resilient member is bent with the slider in the interference position.

25. The bone plate system of claim 17 wherein the resilient member includes a pin.

26. The bone plate system of claim 17 wherein the resilient member extends between the opposite sides of the slider and the supports of the bone plate body.

27. The bone plate system of claim 16 wherein the bone plate body includes an opening in the upper surface extending laterally from the throughbore; and
wherein the slider has a portion in the opening of the bone plate body with the slider in the interference position and the clearance position.

28. A bone plate system comprising:
a bone plate body having an upper surface and a lower surface;
a throughbore of the bone plate body extending between the upper and lower surfaces of the bone plate body along a central, longitudinal axis of the throughbore;
a bone screw having a head portion and a threaded shank portion, the threaded shank portion configured to be advanced into the throughbore and driven into bone;
a slider slidably connected to the bone plate body to contact the bone screw as the bone screw is advanced into the throughbore, the slider configured to be slid along a path by the bone screw from a laterally inward, interference position wherein the slider inhibits bone screw back out from the throughbore to a laterally outward, clearance position wherein the slider permits the bone screw head portion to be advanced into the throughbore and seated against the bone plate body;
supports of the bone plate body on opposite sides of the slider and having a minimum width therebetween transverse to the path of the slider;
a resilient member assembled with the slider and having a maximum dimension when unloaded that is greater than the minimum width between the supports of the bone plate body;
the slider configured to deflect a center portion of the resilient member between the supports of the bone plate body and along the path of the slider as the bone screw contacts the slider and shifts the slider from the laterally inward, interference position to the laterally outward, clearance position; and
side portions of the resilient member on opposite sides of the center portion configured to contact the supports of the bone plate body with the slider in the laterally outward, clearance position and urge the slider toward the laterally inward, interference position upon the bone screw head portion seating against the bone plate body;
wherein the resilient member extends between the opposite sides of the slider and the supports of the bone plate body;
wherein the bone plate body includes an undercut that opens to the throughbore and the supports, the slider having a portion in the undercut and the side portions of the resilient member extending in the undercut.

\* \* \* \* \*